(12) United States Patent
Bellussi et al.

(10) Patent No.: US 8,110,692 B2
(45) Date of Patent: Feb. 7, 2012

(54) ORGANIC-INORGANIC HYBRID SILICATES AND METAL-SILICATES HAVING AN ORDERED STRUCTURE

(75) Inventors: Giuseppe Bellussi, Piacenza (IT); Angela Carati, San Giuliano Milanese (IT); Caterina Rizzo, San Donato Milanese (IT); Urbano Diaz Morales, Valencia (ES); Stefano Zanardi, Pavia (IT); Wallace O'Neil Parker, Peschiera Borromeo (IT); Roberto Millini, Cerro al Lambro (IT)

(73) Assignee: ENI S.p.A., Rome (IT)

( * ) Notice: Subject to any disclaimer, the term of this patent is extended or adjusted under 35 U.S.C. 154(b) by 461 days.

(21) Appl. No.: 12/376,704

(22) PCT Filed: Aug. 3, 2007

(86) PCT No.: PCT/EP2007/007132
§ 371 (c)(1),
(2), (4) Date: Apr. 29, 2009

(87) PCT Pub. No.: WO2008/017513
PCT Pub. Date: Feb. 14, 2008

(65) Prior Publication Data
US 2010/0191009 A1    Jul. 29, 2010

(30) Foreign Application Priority Data

Aug. 7, 2006  (IT) .............................. MI2006A1588
Feb. 16, 2007  (IT) .............................. MI2007A0303

(51) Int. Cl.
*C07F 7/18*    (2006.01)
*C07F 7/02*    (2006.01)

(52) U.S. Cl. ............................................ 556/9; 556/173
(58) Field of Classification Search ............... 556/9, 173
See application file for complete search history.

(56) References Cited

OTHER PUBLICATIONS

Loy, Douglas A., "Sol-Gel Processing of Hybrid Organic-Inorganic Materials Based on Polysilsesquioxanes", Hybrid Materials, Synthesis, Characterization, and Applications, pp. 225-254, XP-002447622, (2007).
Choi, Kyung M., "A chemical strategy to improve the fluorescence environments of erbium-ions doped into organically modified hybrid glasses for laser amplifier applications", Materials Chemistry and Physics, Elsevier, vol. 103, pp. 176-182, XP-002447615, (2007).
Melde, Brian J. et al., "Mesoporous Sieves with Unified Hybrid Inorganic/Organic Frameworks", Chem. Mater., vol. 11, No. 11, pp. 3302-3308, XP-002465121, (1999).

(Continued)

*Primary Examiner* — Porifirio Nazario Gonzalez
(74) *Attorney, Agent, or Firm* — Oblon, Spivak, McClelland, Maier & Neustadt, L.L.P.

(57) ABSTRACT

The present invention relates to new organic-inorganic hybrid silicates and metal-silicates called ECS, characterized by an X-ray powder diffraction pattern with reflections exclusively at angular values higher than 4.0° of 2θ, preferably at angular values higher than 4.7°, and an ordered structure containing structural units having formula (a) wherein R is an organic group: Formula (a) and possibly containing one or more elements T selected from groups III B, IV B, V B and transition metals, with a Si/(Si +T) molar ratio in said structure higher than 0.3 and lower than or equal to 1, wherein Si is the silicon contained in the structural unit (a). A process is also described, starting from disilanes, for the preparation of these materials, which does not include the use of templates or surfactants. These materials can be used as molecular sieves, adsorbents, in the field of catalysis, in the field of electronics, in the field of sensors, in the field of nanotechnologies.

68 Claims, 10 Drawing Sheets

OTHER PUBLICATIONS

Shea, K. J. et al., "Bridged Polysilsesquioxanes Molecular-Engineering Nanostructured Hybrid Organic-Inorganic Materials", Functional Hybrid Materials, pp. 50-85, XP-002447621, (2004).

Sayari, Abdelhamid et al., "New Insights into the Synthesis, Morphology, and Growth of Periodic Mesoporous Organosilicas", Chem. Mater., vol. 12, No. 12, pp. 3857-3863, XP-002465122, (2000).

ASEFA, Tewodros et al., "Periodic mesoporous organosilicas with organic groups inside the channel walls", Nature, Letters to Nature, vol. 402, pp. 867-871, XP-002465123, (1999).

Inagaki, Shinji et al., "Novel Mesoporous Materials with a Uniform Distribution of Organic Groups and Inorganic Oxide in Their Frameworks", J. Am. Chem. Soc., vol. 121, pp. 9611-9614, XP-002465124, (1999).

Choi, Kyung M. et al., "Organic/Inorganic Hybrid Silicate Materials for Optical Applications; Highly Fluorinated Hybrid Glasses Doped with (Erbium-ions/CdSe nanoparticles) for Laser Amplifier Material", Mater. Res. Soc. Symp. Proc., vol. 846, pp. DD8.7.1 to DD8.7.5, XP-002447616, (2005).

Yan, Bing et al., "Molecular assembly and photoluminescence of novel rare earth/inorganic/polymeric hybrid materials with functional covalent linkages", Materials Letters, Elsevier, vol. 60, pp. 3063-3067, XP-002447617, (2006).

ORGANIC-INORGANIC HYBRID SILICATES AND METAL-SILICATES HAVING AN ORDERED STRUCTURE

BACKGROUND OF THE INVENTION

The present invention relates to organic-inorganic, hybrid silicates and metal-silicates having an ordered structure and a process for the preparation thereof.

Silicates and metal-silicates are a group of compounds which can produce three-dimensional compact or porous (zeolites), lamellar (micas and clays) or linear crystalline structures. Zeolites and clays have been extremely important in the evolution of catalytic processes and for the separation of blends of different molecules. Their properties are correlated with the geometry of the crystalline structure and chemical composition, which determine the acidic and polar characteristics. Zeolites, in particular, are crystalline-porous solids having a structure consisting of a three-dimensional lattice of TO4 tetrahedra which are connected by means of oxygen atoms, wherein T is a tri- or tetravalent tetrahedral atom, for example Si or Al.

The substitution of Si or Al with other elements, such as Ge, Ti, P, B, Ga and Fe, for example, has allowed the modification of the physical-chemical properties of materials, obtaining products with new properties, used as catalysts or molecular sieves.

Studies aimed at even more deeply modifying the properties of these materials are underway, for synthesizing organic-inorganic hybrids, in which at least a part of the silica precursor consists of mixed silicates containing at least one Si—C bond. In particular, attempts have been made at synthesizing structures of crystalline-porous silicates or metal-silicates containing organic groups inside the lattice, starting from disilane precursors in which an organic group is linked to two silicon atoms.

In Nature 416, 304-307 (Mar. 21, 2002) Inagaki et al. describes the synthesis of an ordered hybrid, mesoporous silicate containing ≡Si—$C_6H_4$—Si≡ groups. This material has a hexagonal pore distribution with a constant lattice of 52.5 Å and walls which delimit the pores with a structural periodicity equal to 7.6 Å along the direction of the channels. The material was synthesized by adding 1,4-bis(triethoxysilyl)benzene to an aqueous solution containing octadecyltrimethylammonium chloride, as surfactant, and soda. The X-ray powder diffraction pattern shows 3 reflections at low angular values (2θ<4.0°), with 2θ=1.94°, 3.40°, 3.48°, corresponding to distances between planes d=45.5, 26.0, 22.9 Å and 4 reflections in the region 10°<2θ<50° (2θ=11.64°, 23.40°, 35.92°, 47.87° corresponding to d=7.6, 3.8, 2.5 and 1.9 Å) A further reflection was localized at about 20.5° of 2θ, but it was large and badly defined.

JP2002-211917-A describes the introduction of at least one ≡Si—R≡Si≡ unit in the structure of known zeolite phases. In particular MFI, LTA, MOR structures are described, wherein a small amount of the oxygen as the bridge between two silicon atoms (≡Si—O—Si≡) is substituted by methylene groups (≡Si—$CH_2$—Si≡). Examples are provided of ratios of silicon bound to the carbon, with respect to the total silicon T/(Q+T) not higher than 10%. In this ratio, heteroatoms other than silicon possibly present in the structure, such as aluminium, are not considered.

The syntheses are carried out using bis-triethoxysilylmethane (BTESM) as silica source, possibly in the presence of tetraethylorthosilicate. The synthesis method used is that used for the synthesis of known zeolite structures and templates are possibly used. Important breakage phenomena of the Si—C bonds are always observed under the synthesis conditions described, therefore only an aliquot of the above bond remains integral in the final structure.

According with this, the $^{29}$Si-MAS-NMR spectra of the samples show a minor signal at −60 ppm, attributed to the presence of Si—C bonds. Furthermore, intense signals are present, also in samples prepared using BTESM only as silica source, attributed to Q4 sites (about −115 ppm) and Q3 (about −105 ppm), corresponding to Si atoms surrounded by four tetrahedra O—$SiO_3$ and three tetrahedra O—$SiO_3$ and an —OH group, respectively. This confirms a considerable breakage of the Si—C bond of the precursor BTESM.

Materials having very different properties with respect to their inorganic correspondents have therefore not been obtained, probably due to the low substitution level of the ≡Si—O—Si≡ groups with ≡Si—$CH_2$Si≡ groups.

New hybrid, organic-inorganic silicates and metal-silicates having an ordered structure have now been found, useful, for example, in the field of catalysis, in the separation of compounds in blends and nanotechnologies.

BRIEF SUMMARY OF THE INVENTION

An object of the present invention therefore relates to new hybrid, organic-inorganic silicates and metal-silicates called ECS (ENI Carbon Silicates) characterized by an X-ray diffractogram having reflections exclusively at angular values higher than 4.0° of 2θ, preferably exclusively at angular values higher than 4.7° of 2θ, and also characterized by an ordered structure containing structural units having formula (a):

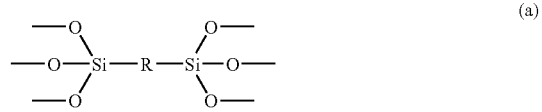

wherein R is an organic group, and which possibly contains one or more elements T selected from elements belonging to groups IIIB, IVB, VB and transition metals, with a Si/(Si+T) molar ratio in said structure higher than 0.3 and lower than or equal to 1, wherein Si is the silicon contained in the structural unit having formula (a).

Hybrid silicates and metal-silicates are a preferred aspect of the present invention, characterized by an X-ray powder diffraction pattern with reflections exclusively at angular values higher than 4.0° of 2θ, preferably exclusively angular values higher than 4.7° of 2θ, and also characterized by an ordered structure containing structural units having formula (a), wherein R is an organic group:

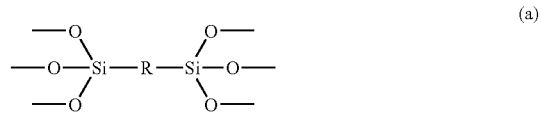

which possibly contains one or more elements T selected from elements belonging to groups IIIB, IVB, VB and transition metals, with a Si/(Si+T) molar ratio in said structure higher than 0.3 and lower than or equal to 1, wherein Si is the silicon contained in the structural unit having formula (a), said (a) units being connected with each other and with the element T, when present, by means of the oxygen atoms.

In accordance with this, the materials of the present invention do not have any reflection at angular values lower than or equal to 4.0° 2θ in the X-ray powder diffraction pattern and, according to a preferred aspect, do not have any reflection at angular values lower than or equal to 4.0° 2θ.

Hybrid silicates and metal-silicates having a Si/(Si+T) ratio higher than or equal to 0.5 and lower than or equal to 1, are particularly preferred.

Hybrid silicates and metal-silicates having a Si/(Si+T) ratio higher than or equal to 0.5 and lower than 1, are even more particularly preferred.

When the Si/(Si+T) ratio is equal to 1 the structure does not contain elements belonging to groups IIIB, IVB, VB and transition metals.

The elements T are tri- or tetravalent, are in tetrahedral coordination and are inserted in the structure by means of four oxygen bridges, forming $TO_4$ units. In particular, in the structure, said $TO_4$ units can be bound by means of these oxygen bridges, not only to the structural units of (a) type, but also to themselves. T is preferably an element selected from Si, Al, Fe, Ti, B, P, Ge, Ga or a mixture thereof. Even more preferably, T is silicon, aluminium, iron or mixtures thereof.

When T is a trivalent element in tetrahedral coordination, the hybrid metal-silicate structure of the present invention will also contain Me cations which will neutralize the corresponding negative charge. The cations can, for example, be cations of alkaline or alkaline-earth metals, cations of lanthanides or mixtures thereof. Me cations from the reagents used in the synthesis can be also contained in silicates and metal-silicates in which T is a tetravalent element.

Hybrid silicates and metal-silicates are therefore a preferred aspect of the present invention, characterized by the following formula (b):

$$SiO_{1.5} \cdot xTO_2 \cdot y/nMe \cdot zC \quad (b)$$

wherein Si is silicon contained in the structural unit (a),
T is at least one element selected from elements belonging to groups IIIB, IVB, VB, and transition metals,
Me is at least one cation having a valence n
C is carbon
x ranges from 0 to 2.3, preferably from 0 to 1
y ranges from 0 to 2.3, preferably from 0 to 1
n is the valence of cation Me
z ranges from 0.5 to 10

The organic group R contained in the structural unit (a) can be a hydrocarbon group having a number of carbon atoms≤20. Said hydrocarbon group can be aliphatic or aromatic, and it can also be substituted by groups containing heteroatoms. The aliphatic groups can be linear or branched and can be both saturated or unsaturated.

R is preferably selected from the following groups:
—$CH_2$—, —$CH_2CH_2$—, linear or branched —$C_3H_6$—, linear or branched —$C_4H_8$—, —$C_6H_4$—, —$CH_2$—($C_6H_4$)—$CH_2$, —$C_2H_4$—($C_6H_4$)—$C_2H_4$—, —($C_6H_4$)—($C_6H_4$)—$CH_2$—($C_6H_4$)—($C_6H_4$)—$CH_2$—, —$C_2H_4$—($C_6H_4$)—($C_6H_4$)—$C_2H_4$—, —CH=CH—, —CH=CH—$CH_2$—, $CH_2$—CH=CH—$CH_2$—.

DETAILED DESCRIPTION OF THE INVENTION

Organic-inorganic silicates and metal-silicates called ECS-1, ECS-2, ECS-3, ECS-4, ECS-5, ECS-6, and ECS-7 are a particular aspect of the present invention.

In particular, silicates and metal-silicates called ECS-4 are characterized by a pore diameter distribution centred within the range of mesopores, preferably within the range of 2-30 nm, with pore walls having an ordered structure. The main X-ray powder diffraction peaks for ECS-4 materials are shown in table 1 and FIG. 1:

TABLE 1

| Nr | 2θ (°) | Intensity [(I/I₀) · 100] |
|---|---|---|
| 1 | 11.6 | 100 |
| 2 | 20.6 | 90 |
| 3 | 23.4 | 76 |
| 4 | 26.9 | 8 |
| 5 | 30.0 | 6 |
| 6 | 31.3 | 5 |
| 7 | 35.5 | 26 |
| 8 | 37.8 | 3 |
| 9 | 44.7 | 3 |
| 10 | 46.9 | 4 |

Preferred ECS-4 structures are those in which Si/(Si+T) is higher than or equal to 0.5 and lower than or equal to 1, even more preferably higher than or equal to 0.5 and lower than 1. Si/(Si+T), for example, can be higher than or equal to 0.9 and lower than or equal to 1.

When the element T is Si, the ratio Si/(Si+T) is higher than 0.5 and lower than 1, for example can be higher or equal to 0.9 and lower than 1. When T is a mixture of Si and Al, or a mixture of Si and Fe, the molar ratio Si/Al or Si/Fe must be higher than or equal to 1, preferably the molar ratio Si/(Si+T) is higher than 0.5 and lower than 1.

Figure 1:
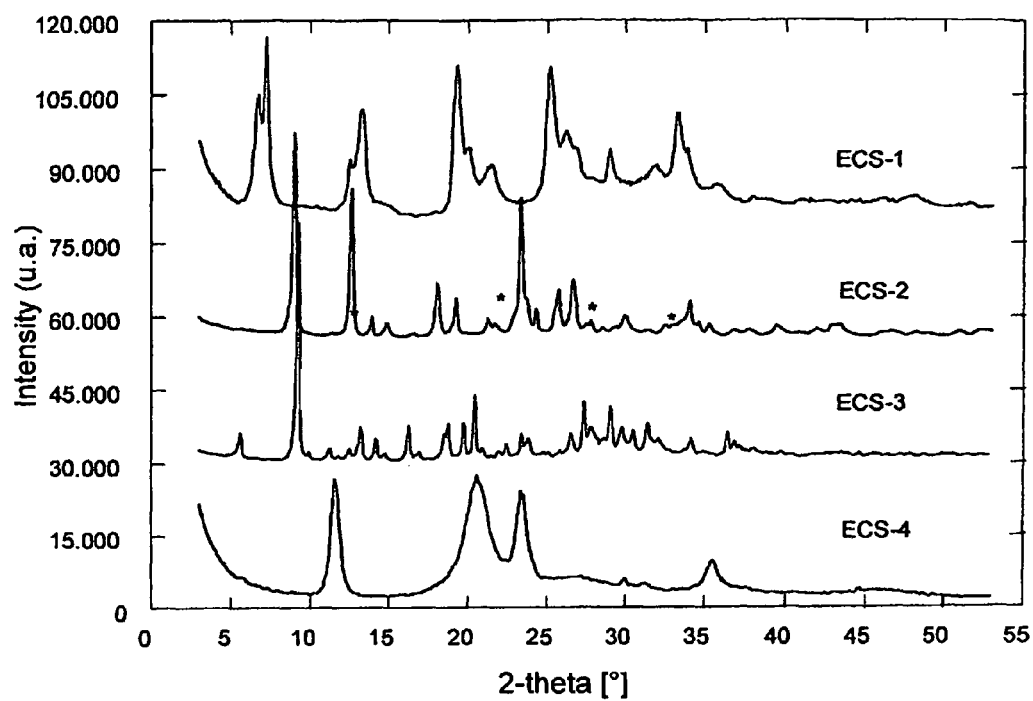
FIG. 1 shows an X-ray powder diffraction pattern of a material ECS-4.

As far as the silicates and metal-silicates called ECS-1 are concerned, these have a crystalline structure and are characterized by a X-ray powder diffraction pattern containing the main reflections shown in table 2 and FIG. 1.

TABLE 2

| Nr | 2θ (°) | Intensity [(I/I₀) · 100] |
|---|---|---|
| 1 | 6.7 | 60 |
| 2 | 7.2 | 100 |
| 3 | 12.5 | 24 |
| 4 | 13.3 | 67 |
| 5 | 19.2 | 82 |
| 6 | 20.1 | 36 |

TABLE 2-continued

| Nr | 2θ (°) | Intensity [(I/I$_0$) · 100] |
|---|---|---|
| 7 | 21.5 | 25 |
| 8 | 25.1 | 84 |
| 9 | 26.2 | 35 |
| 10 | 26.9 | 29 |
| 11 | 29.0 | 33 |
| 12 | 32.0 | 21 |
| 13 | 33.3 | 55 |
| 14 | 34.0 | 18 |
| 15 | 35.9 | 11 |

As far as crystalline silicates and metal-silicates according to the invention are concerned, called ECS-2, these are characterized by a X-ray powder diffraction pattern containing the main reflections shown in table 3 and FIG. 1:

TABLE 3

| Nr | 2θ (°) | Intensity [(I/I$_0$) · 100] |
|---|---|---|
| 1 | 9.0 | 100 |
| 2 | 12.6 | 71 |
| 3 | 13.9 | 2 |
| 4 | 14.9 | 5 |
| 5 | 18.0 | 18 |
| 6 | 19.2 | 12 |
| 7 | 21.3 | 6 |
| 8 | 23.3 | 44 |
| 9 | 23.8 | 7 |
| 10 | 24.3 | 7 |
| 11 | 25.5 | 6 |
| 12 | 25.7 | 13 |
| 13 | 26.6 | 18 |
| 14 | 30.0 | 7 |
| 15 | 34.0 | 5 |
| 16 | 39.4 | 5 |

As far as the silicates and metal-silicates called ECS-3 are concerned, these are crystalline and characterized by a X-ray powder diffraction pattern containing the main reflections shown in table 4 and FIG. 1:

TABLE 4

| Nr | 2θ (°) | Intensity [(I/I$_0$) · 100] |
|---|---|---|
| 1 | 5.6 | 10 |
| 2 | 9.3 | 100 |
| 3 | 13.3 | 14 |
| 4 | 14.2 | 9 |
| 5 | 16.3 | 14 |
| 6 | 18.5 | 9 |
| 7 | 18.8 | 14 |
| 8 | 19.8 | 16 |
| 9 | 20.5 | 27 |
| 10 | 22.5 | 5 |
| 11 | 23.4 | 10 |
| 12 | 26.5 | 9 |
| 13 | 27.3 | 23 |
| 14 | 27.7 | 9 |
| 15 | 29.0 | 20 |
| 16 | 29.8 | 9 |
| 17 | 30.5 | 10 |
| 18 | 31.4 | 12 |
| 19 | 32.1 | 6 |
| 20 | 36.4 | 10 |

Figure 3:
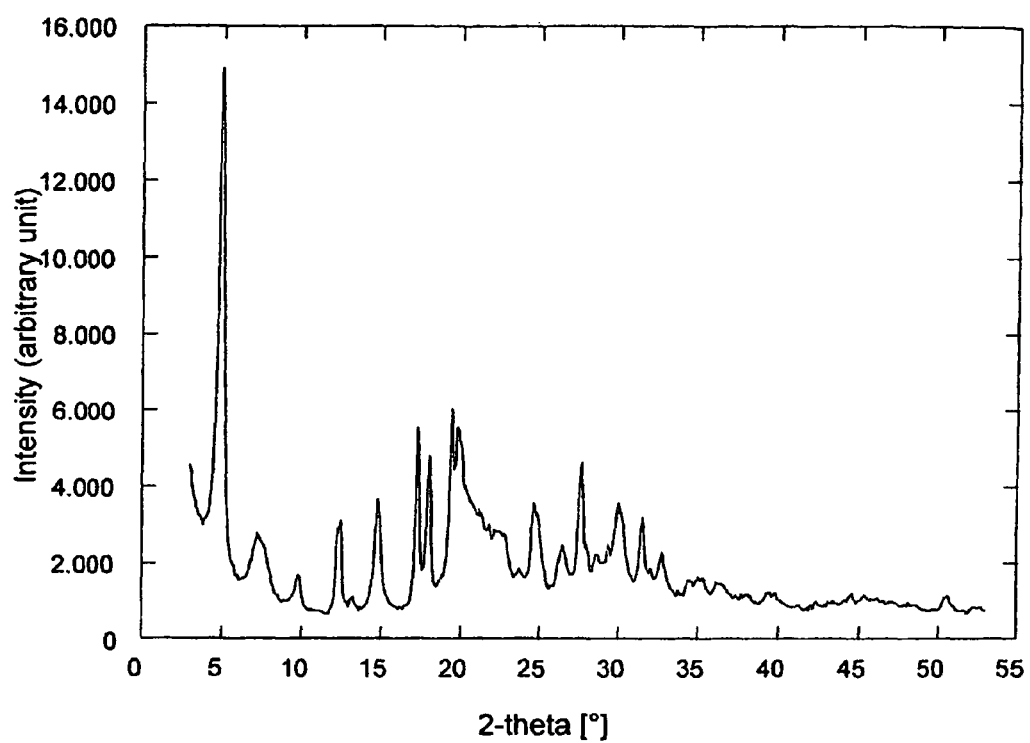
FIG. 3 shows an X-ray diffractogram of a material ECS-5.

As far as the silicates and metal-silicates called ECS-5 are concerned, these are crystalline and characterized by a X-ray powder diffraction pattern containing the main reflections shown in table 5 and FIG. 3:

TABLE 5

| Nr | 2θ (°) | Intensity [(I/I$_0$) · 100] |
|---|---|---|
| 1 | 4.9 | 100 |
| 2 | 7.4 | 12 |
| 3 | 9.8 | 7 |
| 4 | 12.3 | 17 |
| 5 | 12.5 | 19 |
| 6 | 13.2 | 3 |
| 7 | 14.8 | 23 |
| 8 | 17.3 | 35 |
| 9 | 18.0 | 31 |
| 10 | 19.4 | 32 |
| 11 | 19.8 | 20 |
| 12 | 20.8 | 9 |
| 13 | 21.5 | 8 |
| 14 | 22.4 | 9 |
| 15 | 22.9 | 6 |
| 16 | 23.7 | 3 |
| 17 | 24.6 | 7 |
| 18 | 24.8 | 10 |
| 19 | 26.5 | 8 |
| 20 | 27.6 | 25 |
| 21 | 28.0 | 5 |
| 22 | 28.7 | 7 |
| 23 | 29.4 | 7 |
| 24 | 29.9 | 8 |
| 25 | 30.2 | 10 |
| 26 | 31.5 | 15 |
| 27 | 32.1 | 3 |
| 28 | 32.8 | 8 |

Figure 5:
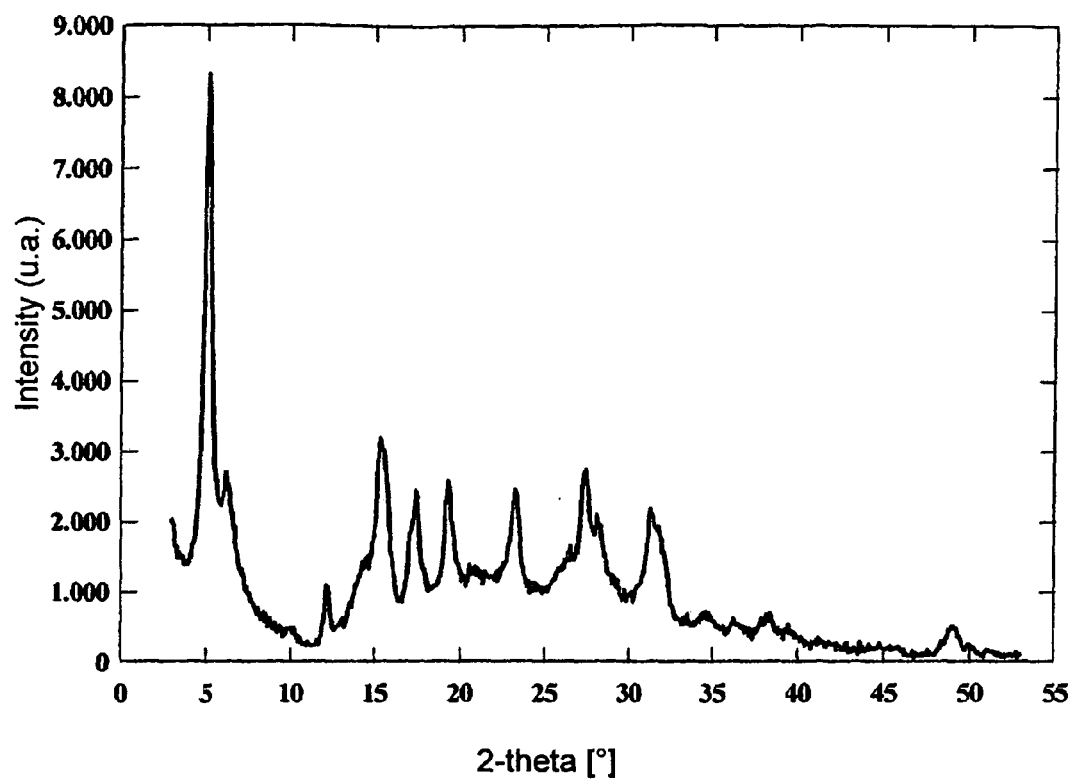
FIG. 5 shows an X-ray powder diffraction pattern of a material ECS-6.

As far as the silicates and metal-silicates called ECS-6 are concerned, these are crystalline and characterized by a X-ray powder diffraction pattern containing the main reflections shown in table 6 and FIG. 5:

TABLE 6

| Nr | 2θ (°) | Intensity [(I/I$_0$) · 100] |
|---|---|---|
| 1 | 5.1 | 100 |
| 2 | 6.2 | 19 |
| 3 | 12.2 | 12 |
| 4 | 14.3 | 7 |
| 5 | 15.5 | 36 |
| 6 | 17.1 | 11 |
| 7 | 17.5 | 20 |
| 8 | 19.3 | 22 |
| 9 | 20.5 | 1 |
| 10 | 21.3 | 2 |
| 11 | 23.3 | 20 |
| 12 | 25.9 | 2 |
| 13 | 26.4 | 5 |
| 14 | 27.4 | 24 |
| 15 | 28.2 | 14 |
| 16 | 31.3 | 17 |
| 17 | 31.9 | 12 |
| 18 | 32.2 | 4 |
| 19 | 34.8 | 3 |
| 20 | 38.3 | 4 |
| 21 | 39.6 | 2 |
| 22 | 49.1 | 6 |

Figure 7:
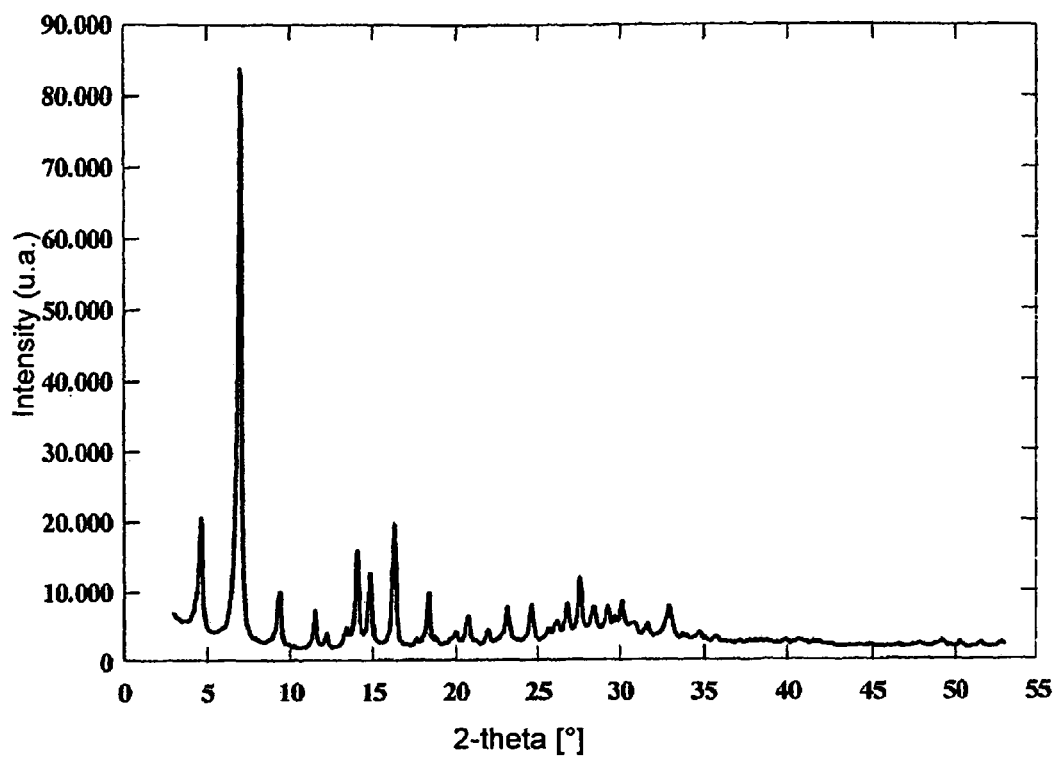
FIG. 7 shows an X-ray powder diffraction pattern of a material ECS-7.

As far as the silicates and metal-silicates called ECS-7 are concerned, these are crystalline and characterized by a X-ray powder diffraction pattern containing the main reflections shown in table 7 and FIG. 7:

TABLE 7

| Nr | 2θ (°) | Intensity [(I/I₀) · 100] |
|----|--------|--------------------------|
| 1  | 4.6    | 20  |
| 2  | 7.0    | 100 |
| 3  | 9.3    | 11  |
| 4  | 11.5   | 7   |
| 5  | 12.2   | 3   |
| 6  | 13.4   | 3   |
| 7  | 14.1   | 18  |
| 8  | 14.8   | 14  |
| 9  | 16.3   | 23  |
| 10 | 18.1   | 2   |
| 11 | 18.3   | 10  |
| 12 | 20.7   | 3   |
| 13 | 20.8   | 4   |
| 14 | 22.0   | 3   |
| 15 | 23.1   | 7   |
| 16 | 24.6   | 7   |
| 17 | 25.6   | 2   |
| 18 | 26.0   | 2   |
| 19 | 26.2   | 3   |
| 20 | 26.8   | 6   |
| 21 | 27.5   | 11  |
| 22 | 28.4   | 6   |
| 23 | 29.2   | 5   |
| 24 | 29.7   | 3   |
| 25 | 30.1   | 6   |
| 26 | 33.0   | 6   |

Structures of the ECS-1, ECS-2, ECS-3, ECS-5, ECS-6 and ECS-7 type in which Si/(Si+T) is higher or equal to 0.5 and lower than or equal to 0.9, more in particular those in which the element T is silicon, aluminium or iron, are preferred.

The X-ray powder diffraction pattern of the materials ECS-1, ECS-2, ECS-3, ECS-4, ECS-5, ECS-6 and ECS-7 mentioned above, were all registered by means of a vertical goniometer equipped with an electronic impulse counting system and using CuKα radiation (λ=1.54178 Å).

The analysis by means of $^{29}$Si-MAS-NMR of the hybrid silicates and metal-silicates of the present invention allows the presence of Si—C bonds to be revealed. It is known, in fact, that in $^{29}$Si-MAS-NMR spectroscopy, the chemical shift of sites of the Si(OT)$_{4-x}$(OH)$_x$ type (where T=Si or Al and x ranges from 0 to 3), is within the range of −90 and −120 ppm (G. Engelhardt, D. Michel, "High-resolution Solid-State NMR of silicates and zeolites", Wiley, New York, 1987, pp 148-149) whereas the chemical shift of sites of the C—Si (OT)$_{3-x}$(OH)$_x$ type (where x ranges from 0 to 2), i.e. silicon atoms bound to a carbon atom, is lower, in absolute value, than −90 ppm, ranges, for example, from −50 and −90 ppm (S. Inakagy, S. Guan, T. Ohsuna, O. Terasaki, Nature, Vol. 416, Mar. 21, 2002, page 304). According to the above, the hybrid, organic-inorganic silicates and metal-silicates of the present invention, prepared using disilanes as silicon source, show, upon $^{29}$Si-MAS-NMR analysis, signals whose chemical shifts fall to absolute values lower than −90 ppm, in particular between −40 and −90 ppm, preferably between −50 and −90 ppm.

Figure 2:
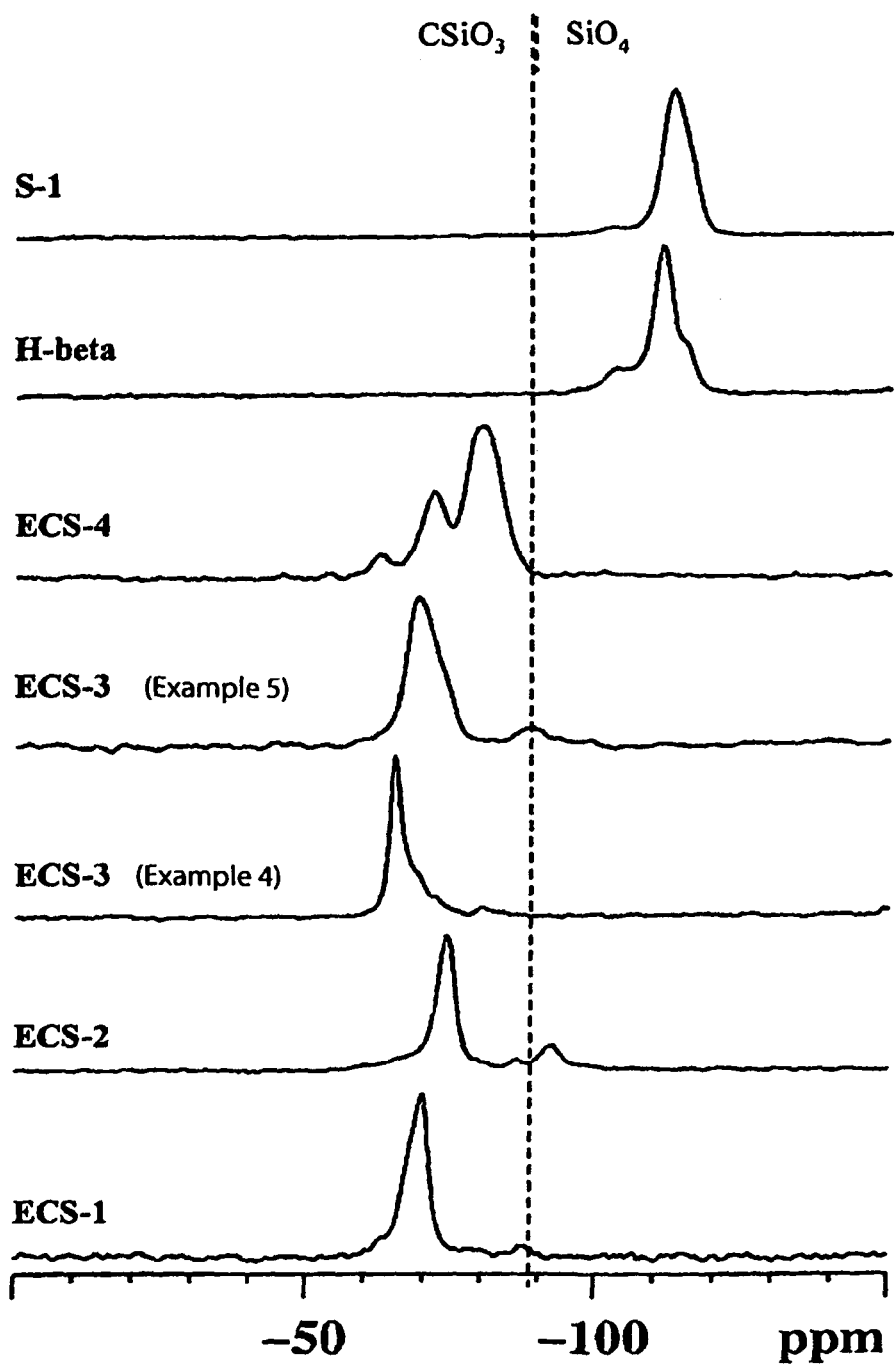
FIG. 2 shows $^{29}$Si-MAS-NMR spectra of hybrid silicates and metal-silicates of materials ECS-1, ECS-2, ECS-3, and ECS-4.
Figure 4:
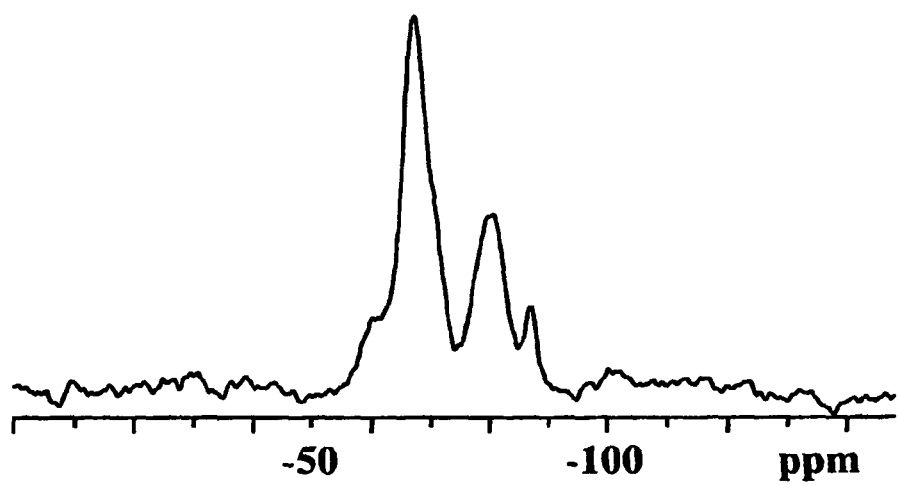
FIG. 4 shows a $^{29}$Si-MAS-NMR spectrum of a material ECS-5.
Figure 6:
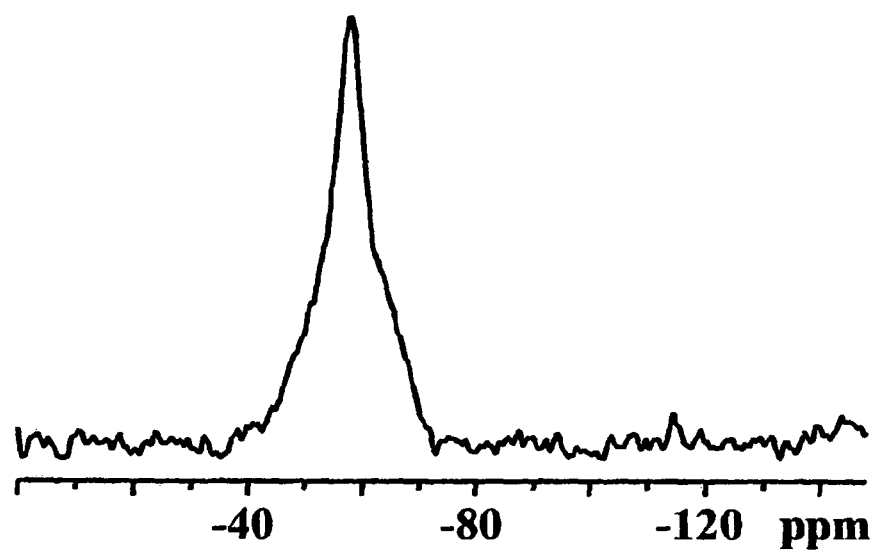
FIG. 6 shows a $^{29}$Si-MAS-NMR spectrum of a material ECS-6.
Figure 8:
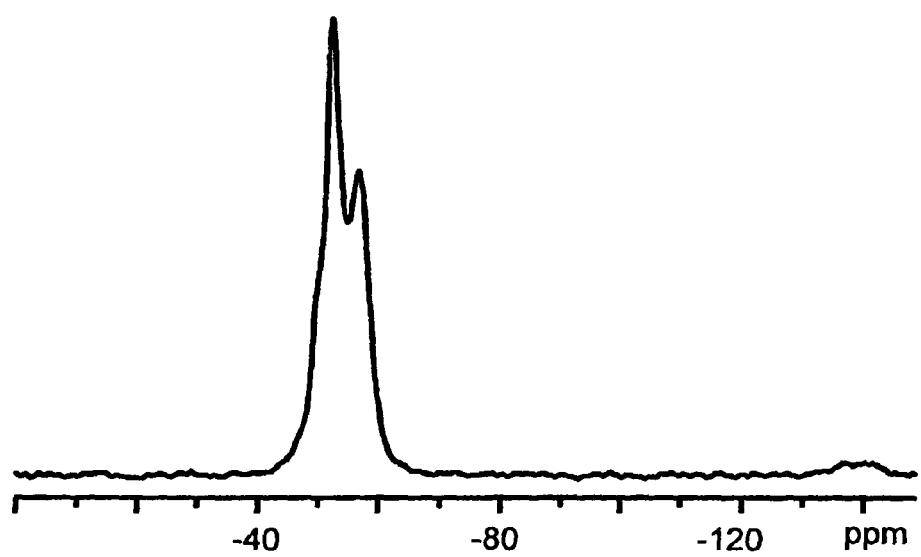
FIG. 8 shows a $^{29}$Si-MAS-NMR spectra of a material ECS-7.

FIG. 2 shows the $^{29}$Si-MAS-NMR spectra of hybrid silicates and metal-silicates, object of the present invention, of the ECS-1, ECS-2, ECS-3, and ECS-4 type, prepared using disilanes alone as silicon source, and compared with spectra of traditional Zeolites: an S-1 silicalite, zeolite of the MFI family and a beta zeolite (Si/Al=12), belonging to the BEA family. FIGS. 4, 6 and 8 show the $^{29}$Si-MAS-NMR spectrum of the hybrid metal-silicate, object of the present invention of the type ECS-5, ECS-6 and ECS-7, respectively.

As can be seen in these figures, the chemical shifts of compounds containing tetrahedral SiO$_4$ only, as in the case of S-1 silicalite or Beta zeolite, range from −100 to −120 ppm. In the case of hybrid silicates and metal-silicates of the ECS-1, ECS-2, ECS-3, ECS-4 and ECS-5 type, object of the present invention, prepared using disilanes alone as silicon source, the signals mainly fall between −50 and −90 ppm, whereas for the materials of the ECS-6 and ECS-7 type, prepared using disilanes alone as silicon source, the signals mainly fall between −40 and −90 ppm, and for all the materials of the present invention, there are very few signals having shifts lower than −90 ppm, indicating that there are only a few silicon atoms involved in four Si—O bonds and almost all the silicon is present as a structural unit (a), the integrity of the Si—C bonds contained in the starting disilane is therefore maintained.

The disilanes used in the preparation of hybrid silicates and metal-silicates of the present invention have the following formula (c):

$$X_3Si—R—SiX_3 \qquad (c)$$

wherein R is an organic group and X is a substituent which can be hydrolyzed.

In accordance with what is specified above, R can be a hydrocarbon group having a number of carbon atoms lower than or equal to 20. Said hydrocarbon group can be aliphatic or aromatic, and can be substituted with groups containing heteroatoms. The aliphatic groups can be linear or branched, saturated or unsaturated.

R is preferably selected from the following groups: —CH$_2$—, —CH$_2$CH$_2$—, linear or branched —C$_3$H$_6$—, linear or branched —C$_4$H$_8$—, —C$_6$H$_4$—, —CH$_2$—(C$_6$H$_4$)—CH$_2$, —C$_2$H$_4$—(C$_6$H$_4$)—C$_2$H$_4$), —(C$_6$H$_4$)—(C$_6$H$_4$)—, —CH$_2$—(C$_6$H$_4$)—(C$_6$H$_4$)—CH$_2$, —C$_2$H$_4$—(C$_6$H$_4$)—(C$_6$H$_4$)—C$_2$H$_4$—, —CH═CH—, —CH═CH—CH$_2$—, CH$_2$—CH═CH—CH$_2$—.

X can be an alkoxide group having the formula —OC$_m$H$_{2m+1}$ wherein m is an integer selected from 1, 2, 3 or 4, or it can be a halogen selected from chlorine, bromine, fluorine and iodine. X is preferably an alkoxide group.

Compounds having formula (c) preferably used are:
(CH$_3$O)$_3$Si—CH$_2$—Si(OCH$_3$)$_3$
(CH$_3$CH$_2$O)$_3$Si—CH$_2$—Si(OCH$_2$CH$_3$)$_3$
(CH$_3$O)$_3$Si—CH$_2$CH$_2$—Si(OCH$_3$)$_3$
(CH$_3$CH$_2$O)$_3$Si—CH$_2$CH$_2$—Si(OCH$_2$CH$_3$)$_3$
(CH$_3$O)$_3$Si—C$_6$H$_4$—Si(OCH$_3$)$_3$
(CH$_3$CH$_2$O)$_3$Si—C$_6$H$_4$—Si(OCH$_2$CH$_3$)$_3$
(CH$_3$O)$_3$Si—CH$_2$—C$_6$H$_4$—CH$_2$—Si(OCH$_3$)$_3$
(CH$_3$CH$_2$O)$_3$Si—CH$_2$—C$_6$H$_4$—CH$_2$—Si(OCH$_2$CH$_3$)$_3$
(CH$_3$O)$_3$Si—C$_6$H$_4$—C$_6$H$_4$—Si(OCH$_3$)$_3$
(CH$_3$CH$_2$O)$_3$Si—C$_6$H$_4$—C$_6$H$_4$—Si(OCH$_2$CH$_3$)$_3$
(CH$_3$O)$_3$Si—CH$_2$—C$_6$H$_4$—C$_6$H$_4$—CH$_2$—Si(OCH$_3$)$_3$
(CH$_3$CH$_2$O)$_3$Si—CH$_2$—C$_6$H$_4$—C$_6$H$_4$—CH$_2$—Si (OCH$_2$CH$_3$)$_3$ In the case of hybrid metal-silicates containing one or more elements of the T type, the reaction mixture will contain a source of each of said elements.

The process for preparing hybrid silicates and metal-silicates of the present invention comprises:
1) adding a disilane having formula (c) to an aqueous mixture containing at least one hydroxide of at least one metal M selected from alkaline and/or alkaline-earth metals and possibly one or more sources of one or more T elements selected from elements belonging to groups IIIB, IVB, VB and transition metals, 2) maintaining the mixture under hydrothermal conditions, under autogenous pressure, for a period of time sufficient for forming a solid material,
3) recovering the solid and drying it.

In step 1), optionally, in addition to the hydroxide of the metal Me, one or more salts of the metal Me can be present.

The mixture of step (1) is prepared by mixing the reagents in the following proportions, expressed as molar ratios:
Si/(Si+T) is higher than 0.3 and lower than or equal to 1 and preferably ranges from 0.5 to 1
$Me^+/Si=0.05-5$
$OH^-/Si=0.05-2$
$H_2O/Si<100$
wherein Si is silicon contained in the disilane having formula (c), T and Me have the respective meanings described above.

Even more preferably, the mixture of step (1) is prepared by mixing the reagents in the following proportions, expressed as molar ratios:
Si/(Si+T) is higher than or equal to 0.5 and lower than 1
$Me^+/Si=0.05-5$
$OH^-/Si=0.05-2$
$H_2O/Si<100$
wherein Si is silicon contained in the disilane having formula (c), T and Me have the respective meanings described above.

For materials of the ECS-1, ECS-2, ECS-3, ECS-5 type, the following molar ratios are preferably used:
$Si/(Si+T)=0.5-0.9$
$Me^+/Si=0.1-2$
$OH^-/Si=0.1-1$
$H_2O/Si=3-50$
wherein disilane 1,4 bis(triethoxysilyl)benzene is preferably used for preparing the ECS-1, ECS-2, ECS-3 materials, and disilane 4,4'bis(triethoxysilyl)1,1'biphenyl is preferably used for preparing the ECS-5 material.

Even more preferably, for the material of the ECS-1 type, the following molar ratios are used:
$Si/(Si+T)=0.5-0.7$
$Me^+/Si=0.1-1.5$
$OH^-/Si=0.1-0.25$
$H_2O/Si=3-50$ Preferably Me=Na and T=Al, Si or Fe and the mixture is maintained, in step (2) under hydrothermal conditions, at autogenous pressure, for a period of 2 to 28 days.

For the material of the ECS-2 type the following molar ratios are preferably used:
Si/(Si+T)=0.7-0.9, even more preferably higher than 0.7 and lower than or equal to 0.9
$Me^+/Si=0.25-1.5$
$OH^-/Si=0.25-1$
$H_2O/Si=3-50$ Preferably Me=Na or Na+Li and T=Al, Si or Fe and the mixture is maintained in step (2) under hydrothermal conditions, at autogenous pressure, for a period of 2 to 50 days.

For the material of the ECS-3 type the following molar ratios are preferably used:
$Si/(Si+T)=0.5-0.9$
$Me^+/Si=0.1-2.0$
$OH^-/Si=0.1-1$
$H_2O/Si=3-50$
wherein Me is a mixture of Na+K and T=Al, Si or Fe and the mixture is maintained in step (2) under hydrothermal conditions, at autogenous pressure, for a period of 2 to 50 days.

For preparing materials of the ECS-4 type the following molar ratios are preferably used:
Si/(Si+T)=0.9-1, preferably higher than 0.9 and lower than 1
$Me^+/Si=0.1-2$
$OH^-/Si=0.1-1$
$H_2O/Si=3-50$ In particular, for preparing materials of the ECS-4 type, when T is Al or Fe, the following molar ratios are preferably used:
Si/(Si+T)=higher than or equal to 0.9 and lower than 1
$Me^+/Si=0.1-2$
$OH^-/Si=0.1-1$
$H_2O/Si=3-50$
and 1,4 bis(triethoxysilyl)benzene is preferably used as disilane.

For preparing materials of the ECS-4 type, when T is Si or a mixture of Si+Al or Si+Fe characterized by a Si/Al or Si/Fe molar ratios≧1, the following molar ratios are also used:
Si/(Si+T)=higher than 0.5 and lower than 1
$Me^+/Si=0.1-2$
$OH^-/Si=0.1-1$
$H_2O/Si=3-50$
and 1,4 bis(triethoxysilyl)benzene is preferably used as disilane. For preparing the ECS-4 materials wherein Si is in such a quantity that Si/Si+T is higher than or equal to 0.9 and lower than 1, the previous synthesis mix is used wherein the ratio Si/Si+T must be higher than or equal to 0.9 and lower than 1.

For preparing the materials of the ECS-5 type, the following molar ratios are preferably used:
$Si/(Si+T)=0.5-0.9$
$Me^+/Si=0.1-2$
$OH^-/Si=0.1-1$
$H_2O/Si=3-50$
and 4,4 bis(triethoxysilyl)1,1'diphenyl is preferably used as disilane.

For preparing the materials of the ECS-6 type, the following molar ratios are preferably used:
$Si/(Si+T)=0.5-0.9$
$Me^+/Si=0.1-2$
$OH^-/Si=0.1-1$
$H_2O/Si=3-50$
and 1,4 bis(triethoxy-silyl)benzene is preferably used as disilane.

For preparing the materials of the ECS-7 type, the following molar ratios are preferably used:
$Si/(Si+T)=0.5-0.9$
$Me^+/Si=0.1-2$
$OH^-/Si=0.1-1$
$H_2O/Si=3-50$
and 1,3 bis(triethoxy-silyl)propane is preferably used as disilane.

A characterizing aspect of the preparation process of the materials of the present invention is the fact of operating in the absence of templates or surfactants.

The sources of the element T, wherein T has the meanings described above and preferably can be Si, Al, Fe, Ti, B, P, Ge, Ga or a mixture thereof, can be the corresponding soluble salts or alkoxides. In particular, when T is silicon, sources which can be conveniently used are tetra-alkylorthosilicate, sodium silicate, colloidal silica; when T is aluminium, sources which can be conveniently used are: aluminium isopropylate, aluminium sulphate, aluminium nitrate or $NaAlO_2$; when T is iron, sources which can be conveniently used are iron ethoxide, iron nitrate, iron sulphate.

The alkaline metal hydroxide is preferably sodium hydroxide and/or potassium hydroxide.

In step (2) of the process of the present invention, the mixture is maintained in an autoclave, under hydrothermal conditions, under autogenous pressure, and possibly under stirring, preferably at a temperature ranging from 70 to 180° C., even more preferably from 80 to 150° C., for a period of time ranging from 1 and 50 days.

At the end of the reaction, the solid phase is separated from the mother blend by means of conventional techniques, for example filtration, washed with demineralised water and subjected to drying, preferably effected at a temperature ranging from 50 to 80° C., for a period of time which is sufficient to eliminate the water completely, or substantially completely, preferably ranging from 2 to 24 hours.

The materials thus obtained can be subjected to ion exchange treatment according to the traditional methods, to obtain, for example, the corresponding acidic form or exchanged with other metals Me, for example alkaline, alkaline-earth metals or lanthanides.

The materials of the present invention can be subjected to shaping, binding or thin layer deposition treatment according to the techniques described in literature.

The materials of the present invention can be used as molecular sieves, absorbers, in the field of catalysis, electronics, sensors and in the nanotechnology sector.

The following examples are provided for a better description of the invention without limiting it.

EXAMPLE 1

Synthesis of a Sample of ECS-4

0.5 g of KOH and 0.14 g of aluminium isopropoxide are dissolved in 11.8 g of demineralised water. 12.0 g of Bis (triethoxy-silyl)benzene, whose chemical formula is provided below, are added to the limpid solution:

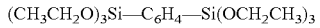

$(CH_3CH_2O)_3Si—C_6H_4—Si(OCH_2CH_3)_3$

The molar ratios between the reagents are as follows:
Si/(Si+Al)=0.99 wherein T=Al
$K^+$/Si=0.15
$OH^-$/Si=0.15
$H_2O$/Si=11
wherein Si is the silicon deriving from Bis(triethoxysilyl) benzene. The blend is left under stirring for about 1 hour at 30-40° C., it is then charged into a stainless steel autoclave subjected to an oscillating movement in an oven heated to 100° C. The blend is left under these hydrothermal reaction conditions for a period of four days.

At the end of the treatment, the autoclave is cooled, the suspension contained therein is filtered and the solid is washed with demineralised water and dried at 60° C. for about two hours. Chemical analysis of the washed and dried sample, has the following molar composition:
1 Si.0.01 Al.0.02 K.2.95 C The X-ray powder diffraction pattern of the material ECS-4 thus obtained, registered by means of a vertical goniometer equipped with an electronic impulse counting system and using CuKα radiation (λ=1.54178 Å), is shown in FIG. 1. It has four well-defined reflections, as shown in Table 1. Compared to the materials described in Inagaki et al., Nature 416, 304-307 (Mar. 21, 2002), the signal at about 20.6 2θ is well-defined, whereas there are no reflections at 2θ≦4.0° and, in particular, there are no reflections also at 2θ≦4.7°.

Figure 9:
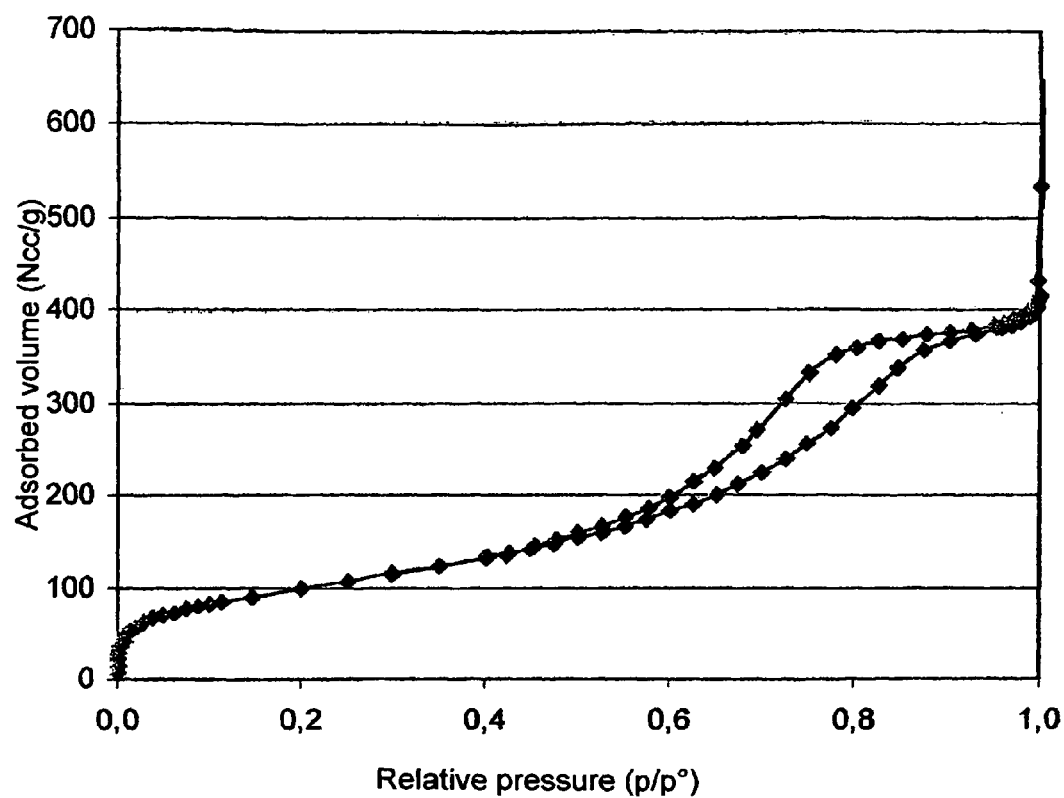
FIG. 9 shows $N_2$ adsorption/desorption isotherms of a material ECS-4.

The morphological characteristics of the material were determined by means of $N_2$ adsorption/desorption isotherms at the temperature of liquid nitrogen, using an ASAP 2010 instrument (Micromeritics). The sample was pre-treated at 60° C. under vacuum for 16 hours. The $N_2$ adsorption/desorption isotherms are of the IV type, with $H_2$ hysteresis, and are shown in FIG. 9 wherein the relative pressure appears in the abscissa (expressed as p/p°) and the volume of $N_2$ absorbed (expressed as Nm/g) appears in the ordinate. The ECS-4 sample has a surface area equal to 360 m²/g and a pore volume of 0.62 ml/g.

Figure 10:
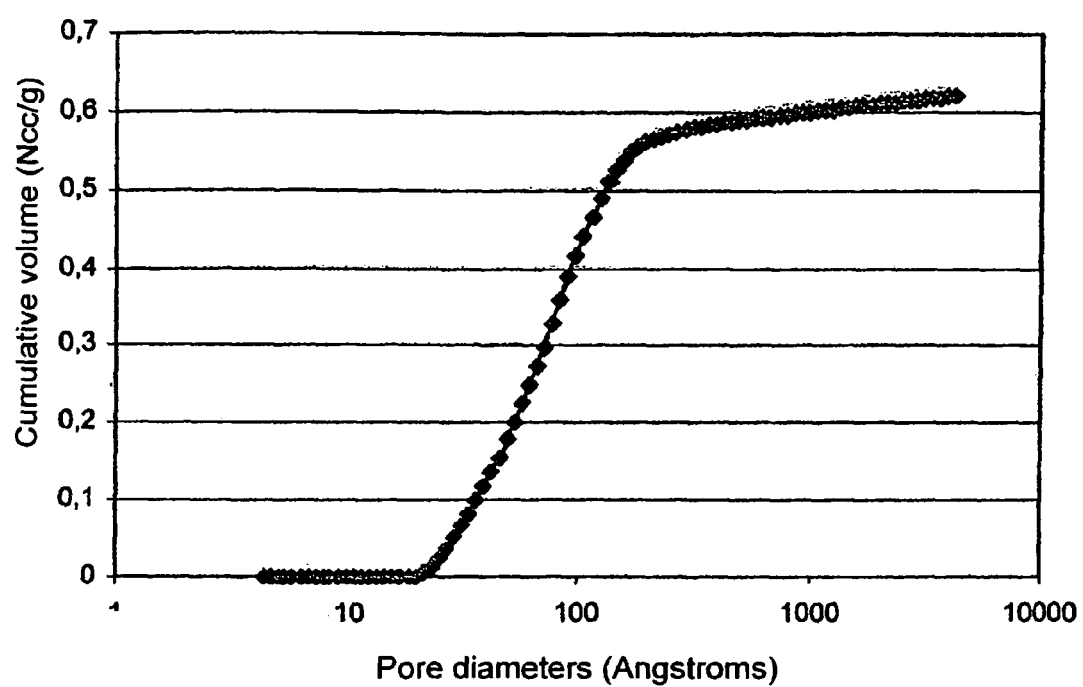
FIG. 10 shows the cumulative pore distribution of a material ECS-4.

A porosity analysis of the sample indicates a pore diameter distribution centred in the field of mesopores, with an average diameter of about 70 Å. The cumulative pore distribution is shown in FIG. 10, the pore diameter (expressed as Angstroms) in the abscissa and the pore cumulative volume (expressed as Nm/g) in the ordinate.

The presence of hysteresis, the absence of reflections at 2θ≦4.0° and, in particular, the absence of reflections at 2θ≦4.7° and the signal definition at about 20.6 2θ demonstrate morphological characteristics quite different with respect to those of the materials described in Inagaki et al., Nature 416, 304-307 (Mar. 21, 2002).

The $^{29}$Si-MAS-NMR spectra of all the examples were collected at 59 MHz (with $^1$H decoupling) with a Bruker ASX-300 instrument, with the samples contained in a 7 mm zirconium sample-holder rotor, rotating at 5 kHz; the chemical shifts were defined on the reference tetrakis(trimethylsilyl) silane at −9.8 and −135.2 ppm.

An analysis of the sample, provided in FIG. 2, shows chemical shifts of the signals between −50 and −90 ppm and there are no signals at shifts lower than −90 ppm, indicating that there are no silicon atoms involved in four Si—O bonds. All the silicon atoms present in the ECS-4 sample are therefore bound to a carbon atom.

EXAMPLE 2

Synthesis of a Sample of ECS-1

0.36 g of NaOH are dissolved in 11.8 g of demineralised water. The limpid solution thus obtained is heated to about 60° C. and 4.88 g of $NaAlO_2$ (54% weight of $Al_2O_3$) are added under vigorous stirring until a limpid, or slightly gelatinous solution, is obtained. The solution is then brought back to room temperature, and 12.0 g of Bis(triethoxysilyl)benzene are added to the reaction environment. The mixture thus obtained has the following composition, expressed as molar ratios:
Si/(Si+Al)=0.54 wherein T=Al
$Na^+$/Si=1.02
$OH^-$/Si=0.15
$H_2O$/Si=11
wherein Si is silicon deriving from Bis(triethoxysilyl)benzene.

The sample is charged into a stainless steel autoclave subjected to an oscillating movement in an oven heated to 100° C. for a period of 7 days.

At the end of the treatment, the autoclave is cooled, the suspension contained therein is filtered and the solid is washed with demineralised water and dried at 60° C. for about two hours. Chemical analysis of the washed and dried sample, shows the following molar composition:
1 Si.0.91 Al.0.73 Na.2.87 C The X-ray powder diffraction pattern is provided in FIG. 1 and Table 2, it shows that the ECS-1 sample is crystalline with a higher order degree than that of the ECS-4 materials. The $^{29}$Si-MAS-NMR spectra provided in FIG. 2, show that the chemical shifts of the signals fall within −50 and −90 ppm, therefore all the silicon present in ECS-1 is involved in C—$SiO_3$ bonds, whereas there are no signals with chemical shifts lower than −90 ppm, which excludes the presence of $SiO_4$ sites.

After pre-treatment at 60° C. under vacuum for 16 hours, the sample has a surface area equal to 350 m²/g and a pore volume of 0.73 ml/g.

EXAMPLE 3

Synthesis of a Sample of ECS-2

0.59 g of NaOH are dissolved in 11.8 g of demineralised water. 2.44 g of NaAlO₂ (54% weight of Al₂O₃) are added to the limpid solution thus obtained, under vigorous stirring until a limpid, or slightly gelatinous solution is obtained. Finally 12.0 g of Bis(triethoxysilyl)benzene are added to the reaction. The mixture thus obtained has the following composition, expressed as molar ratios:
Si/(Si+Al)=0.70 wherein T=Al
Na⁺/Si=0.68
OH⁻/Si=0.25
H₂O/Si=11
wherein Si is silicon deriving from Bis(triethoxysilyl)benzene.

The sample is charged into a stainless steel autoclave subjected to an oscillating movement in an oven heated to 100° C. for a period of 28 days.

At the end of the treatment, the autoclave is cooled, the suspension contained therein is filtered and the solid is washed with demineralised water and dried at 60° C. for about two hours. Chemical analysis of the washed and dried sample, shows the following molar composition:
1.00 Si.0.44 Al.0.53 Na.2.53 C The X-ray powder diffraction pattern is provided in FIG. 1 and Table 3, it shows that the ECS-2 sample is crystalline and mainly consists of the new ECS-2 phase and a smaller amount of a known zeolite, sodalite.

The ²⁹Si-MAS-NMR spectra provided in FIG. 2, show that the silicon present in the sample of ECS-2 is involved in C—SiO₃ bonds, with the exception of a smaller part (about 14%) attributed to SiO₄ sites of the sodalite observed with XRD analysis.

After pre-treatment at 60° C. under vacuum for 16 hours, the sample has surface area equal to 25 m²/g.

EXAMPLE 4

Synthesis of a Sample of ECS-3

0.50 g of KOH are dissolved in 11.8 g of demineralised water. 4.88 g of NaAlO₂ (54% weight of Al₂O₃) are added to the limpid solution thus obtained, under vigorous stirring until a limpid, or slightly gelatinous solution is obtained. Finally, 12.0 g of Bis(triethoxy-silyl)benzene are added to the reaction. The mixture thus obtained has the following composition, expressed as molar ratios:
Si/(Si+Al)=0.54 wherein T=Al
Na⁺/Si=0.87
K⁺/Si=0.15
OH⁻/Si=0.15
H₂O/Si=11
wherein Si is silicon deriving from Bis(triethoxy-silyl)benzene.

The sample is charged into a stainless steel autoclave subjected to an oscillating movement in an oven heated to 100° C. for a period of 7 days.

At the end of the treatment, the autoclave is cooled, the suspension contained therein is filtered and the solid is washed with demineralised water and dried at 60° C. for about two hours. Chemical analysis of the washed and dried sample, shows the following molar composition:
1 Si.0.96 Al.0.72 Na.0.22 K.2.85 C The diffractogram provided in FIG. 1 and Table 4 shows that the ECS-3 sample is crystalline. The ²⁹Si-MAS-NMR spectra provided in FIG. 2, show that the chemical shift of the signals falls between −50 and −90 ppm, therefore all the silicon present in the sample of ECS-3 is involved in C—SiO₃ bonds, whereas there are no signals with chemical shifts lower than −90 ppm and consequently the presence of SiO₄ sites can be excluded.

After pre-treatment at 60° C. under vacuum for 16 hours, the sample has a surface area equal to 105 m²/g and a pore volume of 0.11 ml/g.

EXAMPLE 5

Synthesis of a Sample of ECS-3

The synthesis expressed in example 4 was repeated by crystallizing the reagent mixture at 140° C. for 7 days. The presence of the ECS-3 phase associated with a non-identified secondary phase was observed from the XRD diffractogram.

The ²⁹Si-MAS-NMR spectrum provided in FIG. 2, shows that all the silicon is involved in C—SiO₃ bonds.

EXAMPLE 6

Synthesis of a Sample of ECS-5

0.56 g of NaOH are dissolved in 5.56 g of demineralised water. 1.15 g of NaAlO₂ (54% weight of Al₂O₃) are added to the limpid solution thus obtained, under vigorous stirring until a limpid, or slightly gelatinous solution is obtained. At the end 6.72 g of 4,4'bis(triethoxy-silyl)1,1'diphenyl, whose chemical formula is the following:

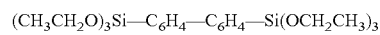

$$(CH_3CH_2O)_3Si—C_6H_4—C_6H_4—Si(OCH_2CH_3)_3$$

are added to the reaction.
The mixture thus obtained has the following composition, expressed as molar ratios:
Si/(Si+Al)=0.70, wherein T=Al
Na⁺/Si=0.93
OH⁻/Si=0.50
H₂O/Si=11
wherein Si is the silicon deriving from 4,4'bis(triethoxy-silyl)1,1'diphenyl.

The sample is charged into a stainless steel autoclave subjected to an oscillating movement, in an oven heated to 100° C. for 14 days.

At the end of the treatment the autoclave is cooled, the suspension contained therein is filtered, the solid is washed with demineralised water and dried at 60° C. for about two hours.

The diffractogram provided in FIG. 3 and Table 5 shows that the ECS-5 sample is crystalline. The ²⁹Si-MAS-NMR spectrum provided in FIG. 4 shows the chemical shifts of the signals between −50 and −90 ppm, therefore in the ECS-5 sample all the silicon present is involved in C—SiO₃ bonds, whereas there are no signals with chemical shifts lower than −90 ppm and consequently the presence of SiO₄ sites can be excluded.

After pre-treatment at 60° C. under vacuum for 16 hours, the sample has a surface area equal to 210 m²/g and a pore volume of 0.56 ml/g.

EXAMPLE 7

Synthesis of a Sample of ECS-6

0.36 g of NaOH are dissolved in 11.81 g of demineralised water. The limpid solution thus obtained is heated to about 60° C. and 4.88 g of NaAlO$_2$ (54§; weight of Al$_2$O$_3$) are added, under vigorous stirring until a limpid, or slightly gelatinous solution is obtained. The solution is brought back to room temperature and finally 11.15 g of 1,4 bis(triethoxy-silyl)benzene are added to the reaction. The mixture thus obtained has the following composition, expressed as molar ratios:
Si/(Si+Al)=0.70 wherein T=Al
Na$^+$/Si=1.02
OH$^-$/Si=0.15
H$_2$O/Si=11
wherein Si is silicon deriving from 1,4 bis(triethoxy-silyl) benzene.

The sample is charged into a stainless steel autoclave subjected to an oscillating movement in an oven heated to 100° C. for a period of 14 days.

At the end of the treatment, the autoclave is cooled, the suspension contained therein is filtered and the solid is washed with demineralised water and dried at 60° C. for about two hours.

The X-ray powder diffraction pattern is provided in FIG. 5 and Table 6, it shows that the ECS-6 is crystalline.

The $^{29}$Si-MAS-NMR spectra provided in FIG. 6, show that the chemical shifts of the signals fall between −40 and −90 ppm, therefore all the silicon present in the sample of ECS-6 is involved in C—SiO$_3$ bonds, and there are no signals with the chemical shifts lower than −90 ppm, therefore the presence of sites SiO$_4$ can be excluded.

After pre-treatment at 60° C. under vacuum for 16 hours, the sample has surface area equal to 25 m$^2$/g.

At the end of the treatment the autoclave is cooled down, the suspension contained therein is filtered, the solid is washed with demineralised water and dried at about 60° C. for about two hours.

The X-ray powder diffraction pattern is provided in FIG. 5 and Table 6, and it shows that the sample ECS-6 is crystalline.

The $^{29}$Si-MAS-NMR spectra provided in FIG. 6, show that the chemical shifts of the signals fall between −40 and −90 ppm, therefore all the silicon present in the sample of ECS-6 is involved in C—SiO$_3$ bonds, and there are no signals with the chemical shifts lower than −90 ppm, therefore the presence of sites SiO$_4$ can be excluded.

The sample, after treatment at 60° C. under vacuum for 16 hours, presents a surface area equal to 25 m$^2$/g.

EXAMPLE 8

Synthesis of a Sample of ECS-7

0.20 g of NaOH are dissolved in 6.47 g of demineralised water. The limpid solution thus obtained is heated to about 60° C. and 2.68 g of NaAlO$_2$ (54% weight of Al$_2$O$_3$) are added, under vigorous stirring until a limpid, or slightly gelatinous solution, is obtained. The solution is brought back to room temperature and finally 4.65 g of bis(triethoxy-silyl)propane are added to the reaction. The mixture thus obtained has the following composition, expressed as molar ratios:
Si/(Si+Al)=0.54 wherein T=Al
Na$^+$/Si=1.02
OH$^-$/Si=0.15
H$_2$O/Si=11
wherein Si is silicon deriving from bis(triethoxy-silyl)propane.

The sample is charged into a stainless steel autoclave subjected to an oscillating movement in an oven heated to 100° C. for a period of 7 days.

At the end of the treatment, the autoclave is cooled, the suspension contained therein is filtered and the solid is washed with demineralised water and dried at 60° C. for about two hours.

The X-ray powder diffraction pattern is provided in FIG. 7 and Table 7, and it shows that the ECS-7 sample is crystalline.

The $^{29}$Si-MAS-NMR spectra provided in FIG. 8, show that the chemical shifts of the signals fall between −40 and −90 ppm, therefore all the silicon present in the sample of ECS-7 is involved in C—SiO$_3$ bonds, and there are no signals with the chemical shifts lower than −90 ppm, therefore the presence of sites SiO$_4$ can be excluded (the peak at −140 ppm is due to the rotation band).

The sample, after treatment at 60° C. under vacuum for 16 hours, presents a surface area equal to 42 m$^2$/g.

EXAMPLE 9

Synthesis of a Sample of ECS-1

0.65 g of NaOH are dissolved in 12.95 g of demineralised water. The limpid solution thus obtained is heated to about 60° C. and 0.54 g of Na$_2$SO$_4$ and 2.69 g of NaAlO$_2$ (54% weight of Al$_2$O$_3$) are added, under vigorous stirring until a limpid, or slightly gelatinous solution, is obtained. The solution is brought back to room temperature and finally 13.18 g of bis(triethoxy-silyl)benzene are added to the reaction. The mixture thus obtained has the following composition, expressed as molar ratios:
Si/(Si+Al)=0.70 wherein T=Al
Na$^+$/Si=0.8
OH$^-$/Si=0.25
H$_2$O/Si=11
wherein Si is silicon deriving from bis(triethoxy-silyl)benzene.

The sample is charged into a stainless steel autoclave subjected to an oscillating movement in an oven heated to 100° C. for a period of 7 days.

At the end of the treatment, the autoclave is cooled, the suspension contained therein is filtered and the solid is washed with demineralised water and dried at 60° C. for about two hours.

The X-ray powder diffraction pattern of the sample obtained is typical of the phase ECS-1.

EXAMPLE 10

Synthesis of a Sample of ECS-2

0.35 g of LiOH are dissolved in 11.81 g of demineralised water. The limpid solution thus obtained is heated to about 60° C. and 2.44 g of NaAlO$_2$ (54% weight of Al$_2$O$_3$) are added, under vigorous stirring until a limpid, or slightly gelatinous solution, is obtained. The solution is brought back to room temperature and finally 12.00 g of bis(triethoxy-silyl)benzene are added to the reaction. The mixture thus obtained has the following composition, expressed as molar ratios:
Si/(Si+Al)=0.70 wherein T=Al
Na/Si=0.43
Li$^+$/Si=0.25
OH$^-$/Si=0.25
H$_2$O/Si=11 wherein Si is silicon deriving from bis(triethoxy-silyl)benzene.

The sample is charged into a stainless steel autoclave subjected to an oscillating movement in an oven heated to 100° C. for a period of 28 days.

At the end of the treatment, the autoclave is cooled, the suspension contained therein is filtered and the solid is washed with demineralised water and dried at 60° C. for about two hours.

The X-ray powder diffraction pattern shows that the sample obtained consists of the ECS-2 phase.

EXAMPLE 11

Synthesis of a Sample of ECS-3

1.17 g of KOH are dissolved in 21.48 g of demineralised water. The limpid solution thus obtained is heated to about 60° C. and 4.88 g of $NaAlO_2$ (54% weight of $Al_2O_3$) are added, under vigorous stirring until a limpid, or slightly gelatinous solution, is obtained. The solution is brought back to room temperature and finally 12.00 g of bis(triethoxysilyl) benzene are added to the reaction. The mixture thus obtained has the following composition, expressed as molar ratios:
Si/(Si+Al)=0.54 wherein T=Al
Na/Si=0.87
K/Si=0.35
$OH^-$/Si=0.35
$H_2O$/Si=20
wherein Si is silicon deriving from bis(triethoxysilyl)benzene.

The sample is subdivided and charged into three stainless steel autoclaves which are introduced into an oven heated to 100° C. and subjected to an oscillating movement for a period of 4, 7 and 14 days.

At the end of the treatment, the autoclaves are cooled, the suspensions contained therein are filtered and the solids are washed with demineralised water and dried at 60° C. for about two hours.

The X-ray powder diffraction pattern shows that all the sample obtained consists of the ECS-3 phase.

EXAMPLE 12

Synthesis of a Sample of ECS-4 Wherein T is a Mix of Al and Si 0.36 g of NaOH are dissolved in 21.48 g of demineralised water. The limpid solution thus obtained is heated to about 60° C. and 2.44 g of $NaAlO_2$ (54% weight of $Al_2O_3$) are added, under vigorous stirring until a limpid, or slightly gelatinous solution, is obtained. The solution is brought back to room temperature and finally a mixture of 5.40 g of tetraethyl orthosilicate (TEOS) and 12.00 g of Bis(triethoxysilyl) benzene is added to the reaction. The mixture thus obtained has the following composition, expressed as molar ratios:
Si/(Si+Al)=0.54 wherein T is an equimolecular mixture of Si deriving from TEOS and Al
$Na^+$/Si=0.58
$OH^-$/Si=0.15
$H_2O$/Si=11
wherein Si is silicon deriving from bis(triethoxysilyl)benzene.

The sample is subdivided and charged into two stainless steel autoclaves subjected to an oscillating movement in an oven heated to 100° C. for a period of 7 and 28 days.

At the end of the treatment, the autoclaves are cooled, the suspensions contained therein are filtered and the solids are washed with demineralised water and dried at 60° C. for about two hours.

The X-ray powder diffraction pattern shows that all the samples obtained consists of the ECS-4 phase. Chemical shifts of the signals of the spectrum $^{29}$Si-MAS-NMR range between −50 and −110 ppm. About 50% moles of Si are $SiO_4$ sites, with signals at −90, −99 and −109 ppm.

EXAMPLE 13

Synthesis of a Sample of ECS-4 Wherein T is Si 0.59 g of NaOH are dissolved in 11.81 g of demineralised water, finally a mix of 5.40 g of tetraethyl ortho silicate (TEOS) and 12.00 g of bis(triethoxysilyl)benzene is added to the reaction. The mixture thus obtained has the following composition, expressed as molar ratios:
Si/(Si+Al)=0.70 wherein T is Si deriving from TEOS
$Na^+$/Si=0.25
$OH^-$/Si=0.25
$H_2O$/Si=11
wherein Si is silicon deriving from bis(triethoxysilyl)benzene.

The sample is subdivided and charged into two stainless steel autoclaves subjected to an oscillating movement in an oven heated to 100° C. for a period of 7 and 28 days.

At the end of the treatment, the autoclaves are cooled, the suspensions contained therein are filtered and the solids are washed with demineralised water and dried at 60° C. for about two hours.

The X-ray powder diffraction pattern shows that all the samples obtained consist of the ECS-4 phase. Chemical shifts of the signals of the spectrum $^{29}$Si-MAS-NMR range from −50 to −110 ppm. About 25% moles of Si are $SiO_4$ sites, with signals at −90, −99 ppm.

EXAMPLE 14

Synthesis of a Sample of ECS-5

0.72 g of KOH are dissolved in 5.06 g of demineralised water. 2.44 g of $NaAlO_2$ (54% weight of $Al_2O_3$) are added to the limpid solution thus obtained, under vigorous stirring until a limpid, or slightly gelatinous solution, is obtained. Finally 6.12 g of 4,4'bis(triethoxysilyl)1,1'biphenyl whose chemical formula is the following:

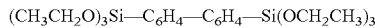

$(CH_3CH_2O)_3Si—C_6H_4—C_6H_4—Si(OCH_2CH_3)_3$ tetraethyl orthosilicate (TEOS) and 12.00 g of Bis(triethoxysilyl)benzene are added to the reaction. The mixture thus obtained has the following composition, expressed as molar ratios:
Si/(Si+Al)=0.54
$Na^+$/Si=0.87
$K^+$/Si=0.50
$OH^-$/Si=0.50
$H_2O/SiO_2$=11
wherein Si is silicon deriving from 4.4°bis(triethoxysilyl)1,1'biphenyl.

The sample is charged into a stainless steel autoclave subjected to an oscillating movement in an oven heated to 100° C. for a period of 14 days.

At the end of the treatment, the autoclave is cooled, the suspensions contained therein are filtered and the solid is washed with demineralised water and dried at 60° C. for about two hours.

The X-ray powder diffraction pattern shows that the sample obtained consists of the ECS-5 phase.

EXAMPLE 15

The adsorption capacity of $CH_4$ at 30° C. between 0.1 and 25 bar was evaluated on the sample of example 1, after pre-treatment at 60° C. for a night, under vacuum, obtaining the values indicated below:

| Adsorption capacity | |
|---|---|
| P (bar) | $CH_4$ (ml/g) |
| 0.1 | 0.2 |
| 4.8 | 6.0 |
| 15.0 | 12.9 |
| 24.9 | 17.6 |

EXAMPLE 16

The adsorption capacity of $CO_2$ at 30° C. between 0.1 and 25 bar was evaluated on the sample of example 1, after pre-treatment at 60° C. for a night, under vacuum, obtaining the values indicated below:

| Adsorption capacity | |
|---|---|
| P (bar) | $CO_2$ (ml/g) |
| 0.1 | 0.2 |
| 4.9 | 23.2 |
| 15.0 | 45.9 |
| 25.0 | 61.1 |

EXAMPLE 17

The adsorption capacity of $H_2$ at 30° C. between 0.1 and 110 bar was evaluated on the sample of example 1, after pre-treatment at 60° C. for a night, under vacuum, obtaining the values indicated below:

| Adsorption capacity at 30° C. | |
|---|---|
| P (bar) | $H_2$ (ml/g) |
| 0.1 | 0.2 |
| 79.8 | 39.5 |
| 109.6 | 45.1 |

EXAMPLE 18

The adsorption capacity of $CO_2$, at 30° C. under pressure, was evaluated on the sample of example 2, after pre-treatment at 60° C. for a night, under vacuum, obtaining, at 15.1 bar of pressure, an adsorption capacity of 47.2 ml/g.

The invention claimed is:

1. An organic-inorganic hybrid silicate or metal-silicate, having an X-ray powder diffraction pattern with reflections exclusively at angular values higher than 4.0° of 2θ, and an ordered structure containing structural units having formula (a) wherein R is an organic group:

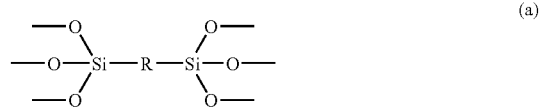

and possibly containing one or more elements T selected from the group consisting of a group III B element, a group IV B element, a group V B element, and a transition metal, with a Si/(Si+T) molar ratio in said structure higher than 0.3 and lower than or equal to 1, wherein Si is the silicon contained in the structural unit of formula (a).

2. The hybrid silicate or metal-silicate according to claim 1, having an X ray diffractogram with reflections exclusively at angular values higher than 4.7° of 2θ.

3. The hybrid silicate or metal-silicate according to claim 1, wherein the (a) units are connected with each other and with the element T, when present, through the oxygen atoms.

4. The hybrid silicate or metal-silicate according to claim 1, having signals in the $^{29}$Si-MAS-NMR spectrum whose chemical shifts fall between −40 and −90 ppm.

5. The hybrid silicate or metal-silicate according to claim 4, having signals in the $^{29}$Si-MAS-NMR spectrum whose chemical shifts essentially fall between −40 and −90 ppm.

6. The hybrid silicate or metal-silicate according to claim 4, whose the chemical shifts fall between −50 and −90 ppm.

7. The hybrid silicate or metal-silicate according to claim 1, wherein the Si/(Si+T) ratio is higher than or equal to 0.5 and lower than or equal to 1.

8. The hybrid silicate or metal-silicate according to claim 1, wherein T is at least one element selected from the group consisting of Si, Al, Fe, Ti, B, P, Ge, and Ga.

9. The hybrid silicate or metal-silicate according to claim 8, wherein T is at least one member selected from the group consisting of silicon, aluminum, and iron.

10. The hybrid silicate or metal-silicate according to claim 1, containing metal cations.

11. The hybrid silicate or metal-silicate according to claim 10, wherein the metal cation is at least one member selected from the group consisting of an alkaline, alkaline-earth metal, and lanthanide.

12. The hybrid silicate or metal-silicate according to claim 3, represented by formula (b):

$$SiO_{1.5} \cdot xTO_2 \cdot y/nMe \cdot zC \qquad (b)$$

wherein Si is the silicon contained in the structural unit (a),
T is at least one element selected from the group consisting of a group IIIB element, a group IVB element, a group VB element, and a transition metal,
Me is at least one cation of having a valence n
C is carbon
x ranges from 0 to 2
y ranges from 0 to 2
n is the valence of the cation Me
z ranges between 0.5 and 10.

13. The hybrid silicate or metal-silicate according to claim 12, wherein x ranges from 0 to 1 and y ranges from 0 to 1.

14. The hybrid silicate or metal-silicate according to claim 1, wherein the organic group R is a hydrocarbon group with a number of carbon atoms lower than or equal to 20.

15. The hybrid silicate or metal-silicate according to claim 14, wherein the hydrocarbon group is an aliphatic group, an aliphatic group substituted with at least one group containing at least one heteroatom, an aromatic group, or an aromatic group substituted with at least one group containing at least one heteroatom.

16. The hybrid silicate or metal-silicate according to claim 15, wherein the aliphatic group is a linear, saturated group; a branched, saturated group; a linear, unsaturated group; or a branched, unsaturated group.

17. The hybrid silicate or metal-silicate according to claim 14, wherein R is selected from the group consisting of:
—$CH_2$—, —$CH_2CH_2$—, linear —$C_3H_6$—, branched —$C_3H_6$—, linear —$C_4H_8$—, branched —$C_4H_8$—, —$C_6H_4$—, —$CH_2$—$(C_6H_4)$—$CH_2$—, —$C_2H_4$—$(C_6H_4)$—$C_2H_4$—, —$(C_6H_4)$—$(C_6H_4)$—, —$CH_2$—$(C_6H_4)$—$(C_6H_4)$—$CH_2$—, —$C_2H_4$—$(C_6H_4)$—$(C_6H_4)$—$C_2H_4$—, —CH=CH—, —CH=CH—$CH_2$—, and $CH_2$—CH=CH—$CH_2$—.

18. The hybrid silicate or metal-silicate according to claim 1, having a pore diameter distribution centered within the range of mesopores, pore walls having an ordered structure, and a X-ray powder diffraction pattern containing the main reflections shown in Table 1 and FIG. 1:

TABLE 1

| Nr | 2θ (°) | Intensity [(I/I$_0$) · 100] |
|---|---|---|
| 1 | 11.6 | 100 |
| 2 | 20.6 | 90 |
| 3 | 23.4 | 76 |
| 4 | 26.9 | 8 |
| 5 | 30.0 | 6 |
| 6 | 31.3 | 5 |
| 7 | 35.5 | 26 |
| 8 | 37.8 | 3 |
| 9 | 44.7 | 3 |
| 10 | 46.9 | 4. |

19. The hybrid silicate or metal-silicate according to claim 18, wherein the pore diameter distribution is within the range of 2-30 nm.

20. The hybrid silicate or metal-silicate according to claim 18, wherein Si/(Si+T) is equal to or higher than 0.5 and lower than or equal to 1.

21. The hybrid silicate or metal-silicate according to claim 20, wherein Si/(Si+T) is higher than or equal to 0.5 and lower than 1.

22. The hybrid silicate or metal-silicate according to claim 20, wherein Si/(Si+T) is higher than or equal to 0.9 and lower than or equal to 1.

23. The hybrid silicate or metal-silicate according to claim 22, wherein T is aluminium, silicon or iron and Si/(Si+T) is higher than or equal to 0.9 and lower than 1.

24. The hybrid silicate or metal-silicate according to claim 21, wherein T is Si, a mixture of Si and Al or a mixture of Si and Fe, and the molar ratio Si/Al and Si/Fe in the mixtures is higher than or equal to 1.

25. The hybrid silicate or metal-silicate according to claim 1 having a crystalline structure and a X-ray powder diffraction pattern containing the main reflections shown in Table 2 and FIG. 1:

TABLE 2

| Nr | 2θ (°) | Intensity [(I/I$_0$) · 100] |
|---|---|---|
| 1 | 6.7 | 60 |
| 2 | 7.2 | 100 |
| 3 | 12.5 | 24 |
| 4 | 13.3 | 67 |
| 5 | 19.2 | 82 |
| 6 | 20.1 | 36 |
| 7 | 21.5 | 25 |
| 8 | 25.1 | 84 |
| 9 | 26.2 | 35 |
| 10 | 26.9 | 29 |
| 11 | 29.0 | 33 |
| 12 | 32.0 | 21 |
| 13 | 33.3 | 55 |
| 14 | 34.0 | 18 |
| 15 | 35.9 | 11. |

26. The hybrid silicate or metal-silicate according to claim 1, having a crystalline structure and a X-ray powder diffraction pattern containing the main reflections shown in Table 3 and FIG. 1:

TABLE 3

| Nr | 2θ (°) | Intensity [(I/I$_0$) · 100] |
|---|---|---|
| 1 | 9.0 | 100 |
| 2 | 12.6 | 71 |
| 3 | 13.9 | 2 |
| 4 | 14.9 | 5 |
| 5 | 18.0 | 18 |
| 6 | 19.2 | 12 |
| 7 | 21.3 | 6 |
| 8 | 23.3 | 44 |
| 9 | 23.8 | 7 |
| 10 | 24.3 | 7 |
| 11 | 25.5 | 6 |
| 12 | 25.7 | 13 |
| 13 | 26.6 | 18 |
| 14 | 30.0 | 7 |
| 15 | 34.0 | 5 |
| 16 | 39.4 | 5. |

27. The hybrid silicate or metal-silicate according to claim 1, having crystalline structure and a X-ray powder diffraction pattern, containing the main reflections shown in table 4 and FIG. 1:

TABLE 4

| Nr | 2θ (°) | Intensity [(I/I$_0$) · 100] |
|---|---|---|
| 1 | 5.6 | 10 |
| 2 | 9.3 | 100 |
| 3 | 13.3 | 14 |
| 4 | 14.2 | 9 |
| 5 | 16.3 | 14 |
| 6 | 18.5 | 9 |
| 7 | 18.8 | 14 |
| 8 | 19.8 | 16 |
| 9 | 20.5 | 27 |
| 10 | 22.5 | 5 |
| 11 | 23.4 | 10 |
| 12 | 26.5 | 9 |
| 13 | 27.3 | 23 |
| 14 | 27.7 | 9 |
| 15 | 29.0 | 20 |
| 16 | 29.8 | 9 |

TABLE 4-continued

| Nr | 2θ (°) | Intensity [(I/I₀) · 100] |
|---|---|---|
| 17 | 30.5 | 10 |
| 18 | 31.4 | 12 |
| 19 | 32.1 | 6 |
| 20 | 36.4 | 10. |

28. The hybrid silicate or metal-silicate according to claim 1, having a crystalline structure and a X-ray powder diffraction pattern containing the main reflections shown in table 5 and FIG. 3:

TABLE 5

| Nr | 2θ (°) | Intensity [(I/I₀) · 100] |
|---|---|---|
| 1 | 4.9 | 100 |
| 2 | 7.4 | 12 |
| 3 | 9.8 | 7 |
| 4 | 12.3 | 17 |
| 5 | 12.5 | 19 |
| 6 | 13.2 | 3 |
| 7 | 14.8 | 23 |
| 8 | 17.3 | 35 |
| 9 | 18.0 | 31 |
| 10 | 19.4 | 32 |
| 11 | 19.8 | 20 |
| 12 | 20.8 | 9 |
| 13 | 21.5 | 8 |
| 14 | 22.4 | 9 |
| 15 | 22.9 | 6 |
| 16 | 23.7 | 3 |
| 17 | 24.6 | 7 |
| 18 | 24.8 | 10 |
| 19 | 26.5 | 8 |
| 20 | 27.6 | 25 |
| 21 | 28.0 | 5 |
| 22 | 28.7 | 7 |
| 23 | 29.4 | 7 |
| 24 | 29.9 | 8 |
| 25 | 30.2 | 10 |
| 26 | 31.5 | 15 |
| 27 | 32.1 | 3 |
| 28 | 32.8 | 8. |

29. The hybrid silicate or metal-silicate according to claim 1, having a crystalline structure and a X-ray powder diffraction pattern containing the main reflections shown in table 6 and FIG. 5:

TABLE 6

| Nr | 2θ (°) | Intensity [(I/I₀) · 100] |
|---|---|---|
| 1 | 5.1 | 100 |
| 2 | 6.2 | 19 |
| 3 | 12.2 | 12 |
| 4 | 14.3 | 7 |
| 5 | 15.5 | 36 |
| 6 | 17.1 | 11 |
| 7 | 17.5 | 20 |
| 8 | 19.3 | 22 |
| 9 | 20.5 | 1 |
| 10 | 21.3 | 2 |
| 11 | 23.3 | 20 |
| 12 | 25.9 | 2 |
| 13 | 26.4 | 5 |
| 14 | 27.4 | 24 |
| 15 | 28.2 | 14 |
| 16 | 31.3 | 17 |
| 17 | 31.9 | 12 |
| 18 | 32.2 | 4 |

TABLE 6-continued

| Nr | 2θ (°) | Intensity [(I/I₀) · 100] |
|---|---|---|
| 19 | 34.8 | 3 |
| 20 | 38.3 | 4 |
| 21 | 39.6 | 2 |
| 22 | 49.1 | 6. |

30. The hybrid silicate or metal-silicate according to claim 1, having a crystalline structure and a X-ray powder diffraction pattern containing the main reflections shown in table 7 and FIG. 7:

TABLE 7

| Nr | 2θ (°) | Intensity [(I/I₀) · 100] |
|---|---|---|
| 1 | 4.6 | 20 |
| 2 | 7.0 | 100 |
| 3 | 9.3 | 11 |
| 4 | 11.5 | 7 |
| 5 | 12.2 | 3 |
| 6 | 13.4 | 3 |
| 7 | 14.1 | 18 |
| 8 | 14.8 | 14 |
| 9 | 16.3 | 23 |
| 10 | 18.1 | 2 |
| 11 | 18.3 | 10 |
| 12 | 20.7 | 3 |
| 13 | 20.8 | 4 |
| 14 | 22.0 | 3 |
| 15 | 23.1 | 7 |
| 16 | 24.6 | 7 |
| 17 | 25.6 | 2 |
| 18 | 26.0 | 2 |
| 19 | 26.2 | 3 |
| 20 | 26.8 | 6 |
| 21 | 27.5 | 11 |
| 22 | 28.4 | 6 |
| 23 | 29.2 | 5 |
| 24 | 29.7 | 3 |
| 25 | 30.1 | 6 |
| 26 | 33.0 | 6. |

31. The hybrid silicate or metal-silicate according to claim 25, wherein the Si/(Si+T) ratio is higher than or equal to 0.5 and lower than or equal to 0.9.

32. The hybrid silicate or metal-silicate according to claim 31 containing an element T which is silicon, aluminium or iron.

33. A process for the preparation of a hybrid silicate or a metal-silicate according to claim 1 comprising:
  1) adding a disilane of formula (c):

$$X_3Si-R-SiX_3 \quad (c)$$

wherein R is an organic group and
  X is a substituent which can be hydrolyzed to an aqueous mixture comprising
  at least one hydroxide of at least one metal Me selected from the group consisting of an alkaline metal and an alkaline-earth metal and
  possibly one or more sources of one or more elements T selected from the group consisting of a group IIIB element, a group IVB element, a group VB element, and a transition metal,
  2) maintaining the mixture obtained under hydrothermal conditions, under autogenous pressure, for a period of time sufficient for forming a solid material,
  3) recovering the solid and drying it.

34. The process according to claim 33, wherein in step (1) one or more salts of the metal Me are present.

35. The process according to claim 33, wherein R is a hydrocarbon group with a number of carbon atoms lower than or equal to 20.

36. The process according to claim 35, wherein the hydrocarbon group is an aliphatic group, an aliphatic group substituted with at least one group containing at least one heteroatom, an aromatic group, or an aromatic group substituted with at least one group containing at least one heteroatom.

37. The process according to claim 36, wherein the aliphatic group is a linear, saturated group; a branched, saturated group; a linear, unsaturated group; or a branched, unsaturated group.

38. The process according to claim 35, wherein R is selected from the group consisting of:
$-CH_2-$, $-CH_2CH_2-$, linear $-C_3H_6-$, branched $-C_3H_6-$, linear $-C_4H_8-$, branched $-C_4H_8-$, $-C_6H_4-$, $-CH_2-(C_6H_4-CH_2$, $-C_2H_4-(C_6H_4)-C_2H_4-$, $-(C_6H_4)-(C_6H_4)-$, $-CH_2-(C_6H_4)-(C_6H_4)-CH_2$, $-C_2H_4-(C_6H_4)-(C_6H_4)-C_2H_4-$, $-CH=CH-$, $-CH=CH-CH_2-$, and $CH_2-CH=CH-CH_2-$.

39. The process according to claim 33, wherein X is
an alkoxide group having the formula $-OC_mH_{2m+1}$, wherein m is an integer selected from 1, 2, 3 or 4, or
a halogen selected from the group consisting of chlorine, fluorine, bromine and iodine.

40. The process according to claim 39, wherein X is an alkoxide group.

41. The process according to claim 33, wherein the compound having formula (c) is selected from the group consisting of:
$(CH_3O)_3Si-C_4H_8-CH_2-C_4H_8-Si(OCH_3)_3$,
$(CH_3CH_2O)_3Si-C_4H_8-CH_2-C_4H_8-Si(OCH_2CH_3)_3$,
$(CH_3O)_3Si-C_4H_8-CH_2CH_2-C_4H_8-Si(OCH_3)_3$,
$(CH_3CH_2O)_3Si-C_4H_8-CH_2CH_2-C_4H_8-Si(OCH_2CH_3)_3$,
$(CH_3O)_3Si-C_4H_8-C_6H_4-C_4H_8-Si(OCH_3)_3$,
$(CH_3CH_2O)_3Si-C_4H_8-C_6H_4-C_4H_8-Si(OCH_2CH_3)_3$,
$(CH_3O)_3Si-C_4H_8-CH_2-C_4H_8-C_6H_4-C_4H_8-CH_2-C_4H_8-Si(OCH_3)_3$,
$(CH_3CH_2O)_3Si-C_4H_8-CH_2-C_4H_8-C_6H_4-C_4H_8-CH_2-C_4H_8Si(OCH_2CH_3)_3$,
$(CH_3O)_3Si-C_4H_8-C_6H_4-C_4H_8-C_6H_4-C_4H_8-Si(OCH_3)_3$,
$(CH_3CH_2O)_3Si-C_4H_8-C_6H_4-C_4H_8-C_6H_4-C_4H_8-Si(OCH_2CH_3)_3$,
$(CH_3O)_3Si-C_4H_8-CH_2-C_4H_8-C_6H_4-C_4H_8-C_6H_4-C_4H_8-CH_2-C_4H_8-Si(OCH_3)_3$ and
$(CH_3CH_2O)_3Si-C_4H_8-CH_2-C_4H_8-C_6H_4-C_4H_8-C_6H_4-C_4H_8-CH_2-C_4H_8-Si(OCH_2CH_3)_3$.

42. The process according to claim 33, wherein the mixture of step (1) is prepared by mixing the reagents in the following proportions, expressed as molar ratios:
Si/(Si+T) is higher than 0.3 and lower than or equal to 1
Me$^+$/Si=0.05-5
OH$^-$/Si=0.05-2
H$_2$O/Si<100
wherein Si is the silicon contained in the disilane of formula (c).

43. The process according to claim 42, wherein the Si/(Si+T) ratio varies from 0.5 to 1.

44. The process according to claim 43, wherein the Si/(Si+T) ratio is higher than or equal to 0.5 and lower than 1.

45. The process according to claim 42, wherein the mixture of step (1) is prepared by mixing the reagents in the following proportions, expressed as molar ratios:
Si/(Si+T)=0.5-0.9
Me$^+$/Si=0.1-2
OH$^-$/Si=0.1-1
H$_2$O/S=3-50.

46. The process according to claim 45 wherein the disilane is 1,4 bis(triethoxysilyl)-benzene.

47. The process according to claim 45, wherein the disilane is 4,4'bis(triethoxysilyl)1,1'diphenyl.

48. The process according to claim 45 wherein the molar ratios are:
Si/(Si+T)=0.5-0.7
Me$^+$/Si=0.1-1.5
OH$^-$/Si=0.1-0.25
H$_2$O/Si=3-50
wherein, Me=Na and T=Al, Si or Fe and the mixture is kept, in step (2), under hydrothermal conditions, at autogenous pressure, for a period of 2 to 28 days.

49. The process according to claim 45 wherein the molar ratios are:
Si/(Si+T)=0.7-0.9
Me$^+$/Si=0.25-1.5
OH$^-$/Si=0.25-1.

50. The process according to claim 49, wherein the Si/(Si+T) ratio is higher than 0.7 and lower than or equal to 0.9.

51. The process according to claim 49, wherein Me=Na or Na+Li, T=Al, Si or Fe and the mixture is maintained, in step (2), under hydrothermal conditions, at autogenous pressure, for a time ranging from 2 to 50 days.

52. The process according to claim 45 wherein the molar ratios are:
Si/(Si+T)=0.5-0.9
Me$^+$/Si=0.1-2.0
OH$^-$/Si=0.1-1
wherein, Me is a mixture of Na+K and T=Al, Si or Fe and the mixture is kept, in step (2), under hydrothermal conditions, at autogenous pressure, for a period ranging from 2 to 50 days.

53. The process according to claim 42 wherein the molar ratios are:
Si/(Si+T)=0.9-1
Me$^+$/Si=0.1-2
OH$^-$/Si=0.1-1
H$_2$O/Si=3-50.

54. The process according to claim 53, wherein the Si/(Si+T) ratio is higher than 0.9 and lower than 1.

55. The process according to claim 53 wherein, T is Al, Si or Fe, and the mixture of step (1) is prepared by mixing the reagents in the following proportions, expressed as molar ratios:
Si/(Si+T)=is higher than or equal to 0.9 and lower than 1
Me+/Si=0.1-2
OH$^-$/Si=0.1-1
H$_2$O/Si=3-50.

56. The process according to claim 55, wherein the disilane is 1,4 bis(triethoxysilyl)benzene.

57. The process according to claim 42, wherein T is Si or a mixture Si+Al or Si+Fe, characterized by a molar ratio Si/Al or Si/Fe≧1, wherein the molar ratios are:
Si/(Si+T)=higher than 0.5, lower than 1
Me$^+$/Si=0.1-2
OH$^-$/Si=0.1-1
H$_2$O/Si=3-50.

58. The process according to claim 57, wherein the disilane present is 1,4 bis(triethoxysilyl)benzene.

59. The process according to claim 42, wherein the molar ratios are:
Si/(Si+T)=0.5-0.9
Me$^+$/Si=0.1-2
OH$^-$/Si=0.1-1
H$_2$O/Si=3-50
and, the disilane is 1,4bis(triethoxysilyl-ethyl)benzene.

60. The process according to claim 42, wherein the molar ratios are:
Si/(Si+T)=0.5-0.9
Me$^+$/Si=0.1-2
OH$^-$/Si=0.1-1
H$_2$O/Si=3-50
and, the disilane is 1,3 bis(triethoxysilyl)propane.

61. The process according to claim 33 wherein in step (1), the corresponding soluble salts or alkoxides are used as sources of the element T.

62. The process according to claim 33 wherein in step (1), the hydroxide of the alkaline metal is at least one of sodium hydroxide, potassium hydroxide, and lithium hydroxide.

63. The process according to claim 33 wherein in step (2), the mixture is maintained in an autoclave, under hydrothermal conditions, at autogenous pressure, and possibly under stirring, at a temperature ranging from 70 to 180° C., for a period of 1 to 50 days.

64. The process according to claim 63, wherein step (2) is effected at a temperature ranging from 80 to 150° C., for a period of 2 to 30 days.

65. The process according to claim 33, wherein the drying is effected at a temperature ranging from 50 to 80° C., for a period of 2 to 24 hours.

66. The hybrid silicate or metal-silicate according to claim 1, in the form of a molecular sieve.

67. The hybrid silicate or metal-silicate according to claim 1, in the form of an absorbent.

68. The hybrid silicate or metal-silicate according to claim 1, wherein the Si/(Si+T) ratio is higher than or equal to 0.5 and lower than 1.

* * * * *